United States Patent
Diana et al.

Patent Number: 5,349,068
Date of Patent: Sep. 20, 1994

[54] 1,2,4-OXADIAZOLYL-PHENOXYALK-YLISOXAZOLES AND THEIR USE AS ANTIVIRAL AGENTS

[75] Inventors: Guy D. Diana, Stephentown; Theodore J. Nitz, Schodack, both of N.Y.

[73] Assignee: Sterling Winthrop Inc., New York, N.Y.

[21] Appl. No.: 869,287

[22] Filed: Apr. 15, 1992

[51] Int. Cl.$^5$ ............................................. C07D 271/06
[52] U.S. Cl. ....................................... 548/131; 548/132; 548/133
[58] Field of Search ................................... 548/131

[56] References Cited

U.S. PATENT DOCUMENTS

| | | | |
|---|---|---|---|
| 4,843,087 | 6/1989 | Diana | 514/374 |
| 4,857,539 | 8/1989 | Diana et al. | 514/378 |
| 4,861,791 | 8/1989 | Diana et al. | 514/374 |
| 4,942,241 | 7/1990 | Diana et al. | 548/131 |
| 4,945,164 | 7/1990 | Diana | 548/247 |

OTHER PUBLICATIONS

Kubel, Monatshepte fur Chemie #113, 781 (1982).
Greene, Protective Groups in Organic Synthesis 2nd ed. pp. 203–205, 431 (1991).

*Primary Examiner*—Robert Gerstl
*Attorney, Agent, or Firm*—Richard A. Hake; Paul E. Dupont; Frederick W. Stonner

[57] ABSTRACT

Compounds of the formula

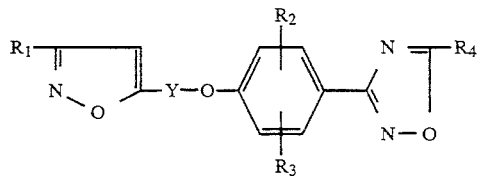

wherein:

$R_1$ is alkyl, alkoxy, hydroxy, cycloalkyl, hydroxyalkyl, alkoxyalkyl or hydroxyalkoxy;

Y is alkylene of 3 to 9 carbon atoms, $R_2$ and $R_3$ independently are hydrogen, alkyl, alkoxy, halo, trifluoromethyl and nitro;

$R_4$ is alkoxy, hydroxy, halomethyl, dihalomethyl, trihalomethyl, cycloalkyl, alkoxycarbonyl, hydroxyalkyl, alkoxyalkyl, alkanecarbonyloxyalkyl, cyano, 2,2,2-trifluoroethyl, (4-methylphenyl)sulfonyloxymethyl, N=Q or CON=Q, where N=Q is amino, alkylamino or dialkylamino; or pharmaceutically acceptable acid-addition salts thereof are useful as antiviral agents.

1 Claim, No Drawings

1,2,4-OXADIAZOLYL-PHENOXYALKYLISOX-AZOLES AND THEIR USE AS ANTIVIRAL AGENTS

BACKGROUND OF THE INVENTION a) Field of the Invention

This invention relates to novel 1,2,4-oxadiazolyl-phenoxyalkylisoxazoles, to methods for the preparation thereof, and compositions and methods for the use thereof as antiviral agents.

b) Information Disclosure Statement

Diana U.S. Pat. No. 4,843,087, issued Jun. 27, 1989, discloses heteryl-phenoxyalkylisoxazoles, wherein the heteryl moiety is an oxazole or an oxazine, which exhibit antiviral activity.

Diana et al. U.S. Pat. No. 4,857,539, issued Aug. 15, 1989, discloses antivirally active compounds of the formula

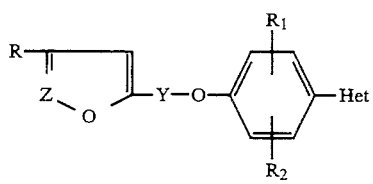

wherein:
Y is an alkylene bridge of 3–9 carbon atoms;
Z is N or HC:
R is hydrogen or lower-alkyl of 1–5 carbon atoms, with the proviso that when Z is N, R is lower-alkyl;
$R_1$ and $R_2$ are hydrogen, halogen, lower-alkyl, lower-alkoxy, nitro, lower-alkoxycarbonyl or trifluoromethyl; and
Het is selected from specified heterocyclic groups. Included in the definition of Het is unsubstituted 1,3,4-oxadiazol-2-yl and unsubstituted 1,2,4-oxadiazol-5-yl.

Diana et al. U.S. Pat. No. 4,861,791, issued Aug. 29, 1989, discloses antivirally active compounds of the formula, inter alia,

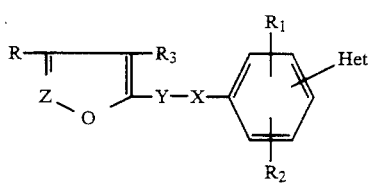

wherein:
Y is an alkylene bridge of 3 to 9 carbon atoms optionally interrupted by one or two oxygen atoms, by cyclohexyl or by an olefinic linkage;
X is O, S, SO or $SO_2$;
Z is N or $R_8$C, where $R_8$ is hydrogen or lower-alkanoyl;
$R_1$ and $R_2$ are selected from the group consisting of hydrogen, lower-alkyl, lower-alkenyl, halogen, nitro, lower-alkoxy, lower-alkylthio, difluoromethyl, trifluoromethyl, amino, lower-alkanoylamino, di-lower-alkylamino, hydroxy, lower-alkenoyl, lower-alkanoyl, hydroxymethyl and carboxy;

R and $R_3$ are each hydrogen or alkyl of 1 to 3 carbon atoms optionally substituted by a member of the group consisting of hydroxy, lower-alkanoyloxy, lower-alkoxy, halo or N=Z', wherein N=Z' is amino, lower-alkanoylamino, lower-alkylamino, di-lower-alkylamino, 1-pyrrolidyl, 1-piperidinyl or 4-morpholinyl; with the proviso that when Z is N, R is other than hydrogen; and
Het is selected from specified heterocyclic groups including unsubstituted 1,3,4-oxadiazol-2-yl.

Diana et al. U.S. Pat. No. 4,942,241, issued Jul. 17, 1990, discloses antivirally active compounds of the formulas

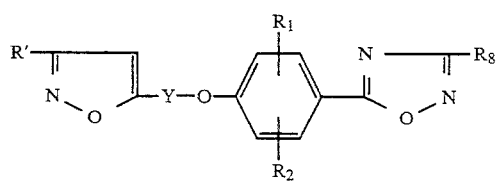

and

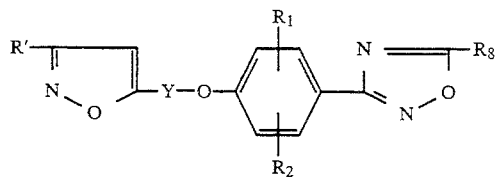

wherein:
Y is an alkylene bridge of 1–9 carbon atoms;
R' is lower-alkyl or hydroxy-lower-alkyl of 1–5 carbon atoms;
$R_1$ and $R_2$ are hydrogen, halogen, lower-alkyl, lower-alkoxy, nitro, lower-alkoxycarbonyl or trifluoromethyl; and
$R_8$ is hydrogen or lower-alkyl of 1–5 carbon atoms.

Diana U.S. Pat. No. 4,945,164, issued Jul. 31, 1990, discloses antivirally active compounds of the formula, inter alia,

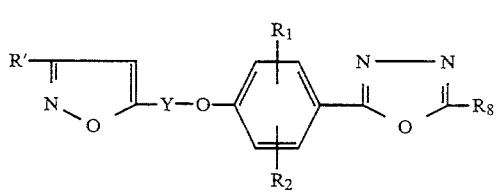

wherein:
Y is an alkylene bridge of 3–9 carbon atoms;
R' is lower-alkyl or hydroxy-lower-alkyl of 1–5 carbon atoms;
$R_1$ and $R_2$ are hydrogen, halogen, lower-alkyl, lower-alkoxy, nitro, lower-alkoxycarbonyl or trifluoromethyl; and
$R_8$ is hydrogen or lower-alkyl of 1–5 carbon atoms.

Commonly assigned G. D. Diana and T. R. Bailey U.S. patent application Ser. No. 07/731,569, filed Jul. 17, 1991, discloses compounds of the formula

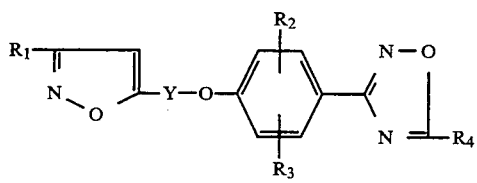

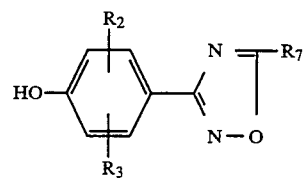

wherein:
Y is alkylene of 3 to 9 carbon atoms;
$R_1$ is lower-alkyl, lower-alkoxy-($C_{1-3}$-alkyl), lower-alkoxycarbonyl, cyclopropyl or trifluoromethyl;
$R_2$ and $R_3$ independently are hydrogen, lower-alkyl, halogen, lower-alkoxy, nitro, trifluoromethyl or hydroxy; and
$R_4$ is hydrogen or lower-alkyl; where lower-alkyl and lower-alkoxy, each occurrence, have from 1-5 carbon atoms;
with the proviso that when $R_1$ is lower-alkyl, at least one of $R_2$ and $R_3$ is hydroxy.

SUMMARY OF THE INVENTION

In one aspect the invention provides a compound of the formula

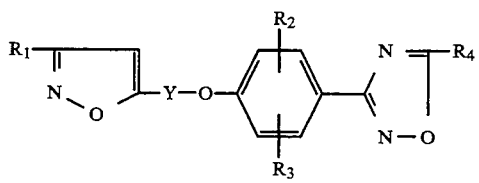

wherein:
$R_1$ is alkyl, alkoxy, hydroxy, cycloalkyl, hydroxyalkyl, alkoxyalkyl or hydroxyalkoxy;
Y is alkylene of 3 to 9 carbon atoms,
$R_2$ and $R_3$ independently are hydrogen, alkyl, alkoxy, halo, trifluoromethyl or nitro;
$R_4$ is alkoxy, hydroxy, halomethyl, dihalomethyl, trihalomethyl, cycloalkyl, alkoxycarbonyl, hydroxyalkyl, alkoxyalkyl, alkanecarbonyloxyalkyl, cyano, 2,2,2-trifluoroethyl, (4-methylphenyl)sulfonyloxymethyl, N=Q or CON=Q, where N=Q is amino, alkylamino or dialkylamino; or a pharmaceutically-acceptable acid-addition salt thereof.

In another aspect the invention provides a compound of the formula

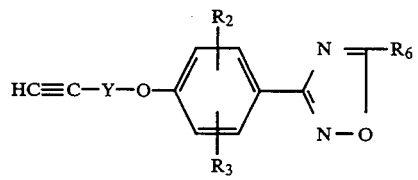

wherein Y, $R_2$ and $R_3$ are as defined above and $R_6$ is alkoxy, fluoromethyl, difluoromethyl, trihalomethyl, cycloalkyl or alkoxyalkyl.

In another aspect the invention provides a compound of the formula wherein $R_2$ and $R_3$ are as defined above and $R_7$ is alkoxy, fluoromethyl, difluoromethyl, trifluoromethyl, cycloalkyl, alkoxyalkyl or cyano.

In other aspects the invention provides compounds of formulas XVII and XXI hereinafter.

In other aspects the invention provides a composition for combatting picornaviruses which comprises an antivirally effective amount of a compound of formula I in admixture with a suitable carrier or diluent and to methods for combatting picornaviruses therewith including combatting a picornaviral infection in a mammalian host.

The compounds of formula I are useful as antipicornaviral agents.

The compounds of formulas III, IV, XVII and XXI are useful as intermediates for the preparation of the compounds of formula I.

DETAILED DESCRIPTION INCLUSIVE OF PREFERRED EMBODIMENTS

Preferred compounds of formula I are those wherein
$R_1$ is $C_{1-3}$-alkyl, $C_{1-3}$-alkoxy, hydroxy, cyclopropyl, hydroxy-$C_{1-3}$-alkyl, $C_{1-3}$-alkoxy-$C_{1-3}$-alkyl or hydroxy-$C_{1-3}$-alkoxy;
Y is alkylene of 3 to 9 carbon atoms, especially 3 to 5 carbon atoms;
$R_2$ and $R_3$ independently are hydrogen, $C_{1-3}$-alkyl, $C_{1-3}$-alkoxy or halo; and
$R_4$ is $C_{1-3}$-alkoxy, hydroxy, halomethyl, dihalomethyl, trihalomethyl, cyclopropyl, $C_{1-3}$-alkoxycarbonyl, hydroxy-$C_{1-3}$-alkyl, $C_{1-3}$-alkoxy-$C_{1-3}$-alkyl, ($C_{1-3}$-alkane)carbonyloxy-$C_{1-3}$-alkyl, cyano, 2,2,2-trifluoroethyl, 4-(methylphenyl)sulfonyloxymethyl, N=Q or CON=Q, where N=Q is amino, $C_{1-3}$-alkylamino or di-($C_{1-3}$-alkyl)amino.

More preferred compounds of formula I are compounds of the formula

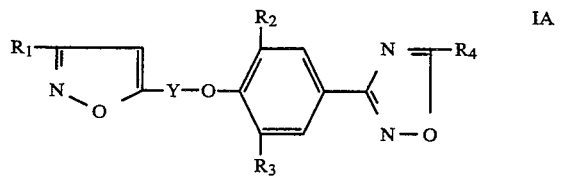

wherein $R_1$, Y, $R_2$, $R_3$ and $R_4$ are as defined above for formula I and especially wherein $R_1$, Y, $R_2$, $R_3$ and $R_4$ are as defined in the previous paragraph for the preferred compounds of formula I.

Especially preferred are the compounds of formula I or IA wherein $R_4$ is $C_{1-3}$-alkoxy, fluoromethyl, dihalomethyl, trihalomethyl, cycloalkyl or $C_{1-3}$-alkoxy-$C_{1-3}$-alkyl, especially trifluoromethyl.

It should be understood that in the compounds of the invention, when the 1,2,4-oxadiazole ring is substituted by hydroxy, amino or alkylamino, they may exist in any of three possible tautomeric forms as follows:

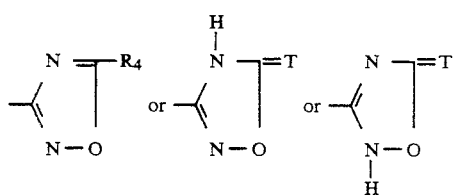

wherein R₄ is hydroxy, amino or alkylamino and T is O, NH or N-alkyl, and such tautomers are within the purview of the invention.

As used herein, unless otherwise specifically defined, alkyl, alkane, alkoxy, cycloalkyl and halo each has the following meaning:

alkyl and alkoxy mean aliphatic radicals, including branched radicals, of from one to five carbon atoms. Thus the alkyl moiety of such radicals include, for example methyl, ethyl, propyl, isopropyl, n-butyl, sec-butyl, t-butyl and pentyl;

alkane means a monovalent aliphatic radical, including branched radicals of from one to four carbon atoms. Thus the alkane moiety of such radical includes, for example, methyl, ethyl, propyl, isopropyl, n-butyl and sec-butyl;

cycloalkyl means an alicyclic radical having from three to six carbon atoms as illustrated by cyclopropyl, cyclobutyl, cyclopentyl and cyclohexyl; and halo means bromo, chloro, iodo or fluoro.

As used herein, in hydroxyalkyl and alkoxyalkyl, the hydroxy and alkoxy groups can occur at any available position of alkyl. Thus hydroxyalkyl and alkoxyalkyl include, for example, hydroxymethyl, 1-hydroxyethyl, 2-hydroxyethyl, 2-hydroxypropyl, 2-hydroxyisopropyl, 2, 3, 4 and 5-hydroxypentyl and the like and corresponding alkyl ethers thereof.

As used herein, in hydroxyalkoxy, the hydroxy group can occur at any available position of alkoxy other than the C-1 position. Thus hydroxyalkoxy includes, for example, 2-hydroxyethoxy, 2-hydroxypropoxy, 2-hydroxyisopropoxy, 2 and 5-hydroxypentoxy and the like.

The compounds of formula I wherein $R_1$ is alkyl, alkoxy, cycloalkyl or alkoxyalkyl, Y, $R_2$ and $R_3$ are as defined hereinbefore, and $R_4$ is hydroxy, halomethyl, dihalomethyl, trihalomethyl, cycloalkyl, alkoxycarbonyl, alkoxyalkyl, alkanecarbonyloxyalkyl or 2,2,2-trifluoroethyl, can be prepared by a process which comprises reacting an amidoxime (N-hydroxycarboximidamide) of the formula

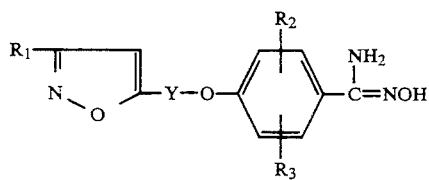

with an acid halide, R₄COX, an alkyl haloformate, ROCOX (in the case where R₄ in formula I is hydroxy), where R is methyl or ethyl, or an acid anhydride, (R₄CO)₂O, where $R_1$, Y, $R_2$, $R_3$ and $R_4$ are as defined above in this paragraph and X is bromo, chloro, fluoro or iodo under anhydrous conditions to form the corresponding compound of formula I. The process involves the following methods. In one method, the amidoxime V is reacted with the acid halide or the acid anhydride in the presence of an organic or inorganic base, e.g., pyridine, triethylamine or potassium carbonate, in an inert solvent, e.g., acetone, methylene chloride, chloroform, toluene or tetrahydrofuran, or in a base which also functions as the solvent, e.g., pyridine, at an elevated temperature (about 40°–130° C.) or at a reduced temperature (about 0°–15° C.). In the latter case an intermediate O-acyl derivative [C(NH₂)=NOC(=O)—(R₄ or OR)] is isolated and heated at a temperature in the range of about 100°–130° C. for a time sufficient for cyclization to the oxadiazole of formula I to occur, generally about 5 minutes to 4 hours. In another method, the amidoxime V is reacted with the acid halide or acid anhydride in an acid which corresponds to the acid halide or acid anhydride at an elevated temperature (about 70°–100° C.).

The compounds of formula I where $R_1$ is alkyl, alkoxy, cycloalkyl or alkoxyalkyl, Y, $R_2$ and $R_3$ are as defined hereinbefore, and $R_4$ is dihalomethyl, trihalomethyl, cycloalkyl, alkoxyalkyl, alkanecarbonyloxyalkyl or 2,2,2-trifluoroethyl can be prepared by a process which comprises reacting amidoxime V with the product obtained by reaction of a carboxylic acid, R₄CO₂H, where $R_1$, Y, $R_2$, $R_3$ and $R_4$ are as defined above in this paragraph, with the coupling agent N,N'-carbonyldiimidazole, prepared as described in the examples, in an inert solvent, e.g., tetrahydrofuran, chloroform, methylene chloride or toluene, at an elevated temperature (about 40°–80° C.) to form the corresponding compound of formula I.

The compounds of formula I wherein $R_1$ is alkyl, alkoxy, cycloalkyl or alkoxyalkyl, Y, $R_2$ and $R_3$ are as defined hereinbefore, and $R_4$ is amino can be prepared by a process which comprises reacting amidoxime V, where $R_1$, Y, $R_2$ and $R_3$ are as defined above in this paragraph, with cyanogen halide, CNX₁, where X₁ is bromo, chloro or iodo, in the presence of a base, e.g., potassium or sodium bicarbonate, in an alcoholic solvent, e.g., ethyl alcohol, at about room temperature to give the compound of formula I where R₄ is amino.

The compounds of formula I where $R_1$ is alkyl, alkoxy, cycloalkyl or alkoxyalkyl, Y, $R_2$ and $R_3$ are as defined hereinbefore and R₄ is CH₂CF₃ can be prepared by reacting amidoxime V where $R_1$ is as defined above in this paragraph and Y, $R_2$ and $R_3$ are as defined hereinbefore, with a ketene 1,3-propanedithiol acetal of the formula

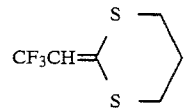

to give the corresponding compound of formula I.

The amidoxime V and ketene 1,3-propanedithiol acetal are reacted in the presence of silver trifluoroacetate in an inert solvent, e.g., tetrahydrofuran, dioxane, dimethylformamide or N-methylpyrrolidinone, at a temperature in the range of from about 60° to about 100° C. Preferably the reaction is carried out in the dark.

The intermediate amidoxime V is prepared according to the following flow sheet:

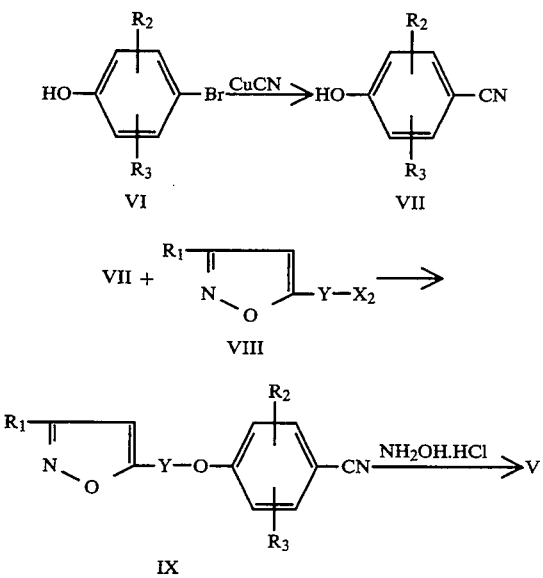

The bromophenol VI reacts with the cuprous cyanide in an inert solvent at an elevated temperature, e.g., in dimethylformamide at reflux temperature to give the cyanophenol VII. The latter is reacted with haloisoxazole VIII, where $X_2$ is chloro, bromo or iodo, in a dry inert solvent, e.g., acetonitrile or N-methylpyrrolidinone, in the presence of a base, e.g., potassium carbonate or sodium hydroxide, optionally in the presence of a catalytic amount of potassium or sodium iodide, at an elevated temperature (50°–120° C.) to give cyano compound IX. The cyano compound IX reacts with the hydroxylamine hydrochloride in the presence of a base, e.g. potassium or sodium carbonate, sodium acetate or sodium hydroxide, in an alcoholic solvent, e.g., ethyl alcohol, at an elevated temperature (50°–150° C.) to give the amidoxime V.

Certain intermediate compounds of formula IX wherein $R_1$ is alkyl, cycloalkyl or alkoxyalkyl and Y, $R_2$ and $R_3$ are as defined hereinbefore can be prepared by reacting the ethinyl compound XII described hereinafter with a nitrile oxide, $R_1C{\equiv}N{\rightarrow}O$, where $R_1$ is as defined above in this paragraph, using a procedure similar to that described hereinafter for the preparation of compound I from the ethinyl compound III.

The intermediate bromophenols of formula VI and cyanophenols of formula VII belong to generically known classes of compounds and are readily prepared by known procedures.

The intermediate haloisoxazoles of formula VIII can be prepared by the procedure described in U.S. Pat. No. 4,843,087, i.e., by reacting an alkali metal derivative of an isoxazole of the formula

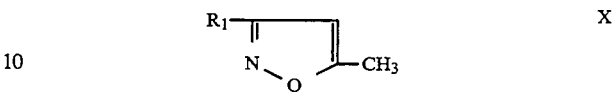

wherein $R_1$ is alkyl, alkoxy, trifluoromethyl, cycloalkyl or alkoxyalkyl, with a dihalide, $X_2$—Y'—$X_2$, where Y' is alkylene of 2 to 8 carbon atoms and $X_2$ is as defined above. The alkali metal derivative is prepared in situ by treating isoxazole X with an organo-alkali metal base such as butyllithium or lithium diisopropylamide under anhydrous conditions.

The compounds of formula I wherein $R_1$ is alkyl, cycloalkyl or alkoxyalkyl, Y, $R_2$ and $R_3$ are as defined hereinbefore, and $R_4$ is alkoxy, trihalomethyl, cycloalkyl, alkoxycarbonyl, alkoxyalkyl or 2,2,2-trifluoroethyl, can be prepared by a process which comprises reacting an ethinyl compound of formula III hereinabove, wherein $R_6$ has the meaning defined above in this paragraph for $R_4$, with a nitrile oxide of the formula $R_1C{\equiv}N{\rightarrow}O$ which is prepared in situ from a hydroxyimino halide of the formula $R_1C(X_3){=}NOH$, where $X_3$ is chlorine or bromine, in the presence of an amine base, e.g., triethylamine, pyridine or N-methylpyrrolidine. The hydroxyimino halides, which may also be prepared in situ, belong to a generically known class of compounds and are readily prepared by conventional procedures, e.g., by reacting the corresponding aldehyde oxime ($R_1C{=}NOH$) with a halogenating agent, e.g., N-chlorosuccinimide or bromine. The process for preparing the compounds of formula I by reacting the ethinyl compound of formula III takes place by heating the reactants in an inert polar solvent, e.g., dimethylformamide or N-methylpyrrolidone, at a temperature in the range of about 20° to about 120° C.

The intermediate ethinyl compounds of formula III are prepared according to the following flow sheet:

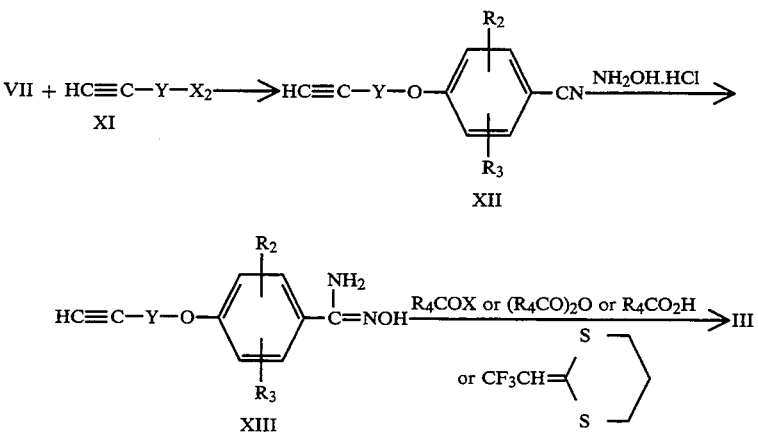

The cyanophenol VII is reacted with haloalkyne XI, where $X_2$ is as defined hereinbefore, using a procedure similar to that described above for the preparation of the cyano compound IX from compounds VII and VIII, to give the ethinyl compound of formula XII.

Ethinyl compound XII is reacted with the hydroxylamine hydrochloride, using a procedure similar to that described above for the preparation of amidoxime V from cyano compound IX, to give the amidoxime of formula XIII. The amidoxime XIII is reacted with the acid halide $R_4COX$, acid anhydride $(R_4CO)_2O$, carboxylic acid $R_4CO_2H$ or

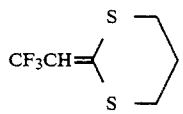

using procedures similar to those described hereinbefore for the preparation of compounds of formula I from amidoxime V.

The haloalkynes of formula XI belong to a generically known class of compounds.

The compounds of formula I where $R_1$ is alkyl, alkoxy, cycloalkyl or alkoxyalkyl, Y, $R_2$ and $R_3$ are as defined hereinbefore, and $R_4$ is alkoxy, trihalomethyl, cycloalkyl, alkoxycarbonyl, alkoxyalkyl or 2,2,2-trifluoroethyl, can be prepared by a process which comprises reacting a phenol of the formula IV above wherein $R_2$ and $R_3$ are as defined hereinbefore and $R_7$ is as defined above in this paragraph for $R_4$, with a haloisoxazole of formula VIII above where $R_1$ is as defined above in this paragraph and Y and $X_2$ are as defined hereinbefore, to give the corresponding compound of formula I. The procedure used is similar to that described above for the preparation of cyano compound IX by reaction of cyanophenol VII and haloisoxazole VIII.

The intermediate haloisoxazole VIII can be prepared as described hereinbefore.

The intermediate phenols of formula IV can be prepared by reacting cyanophenol VII with hydroxylamine hydrochloride, using a procedure similar to that described hereinbefore for the preparation of amidoxime V from cyano compound IX, to give an amidoxime of the formula

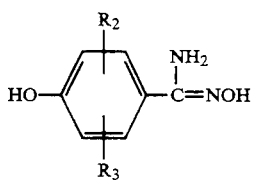

Amidoxime XIV is reacted with $R_4COX$, $(R_4CO)_2O$, $R_4CO_2H$ or

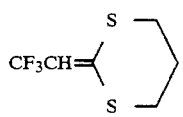

using procedures similar to those described hereinbefore for the preparation of compounds of formula I from amidoxime V, to give the corresponding phenol of formula IV.

The compounds of formula I wherein $R_1$ is hydroxyalkyl, Y, $R_2$ and $R_3$ are as defined hereinbefore, and $R_4$ is dihalomethyl, trihalomethyl, cycloalkyl, alkoxyalkyl, 2,2,2-trifluoroethyl or amino can be prepared from a compound of the formula

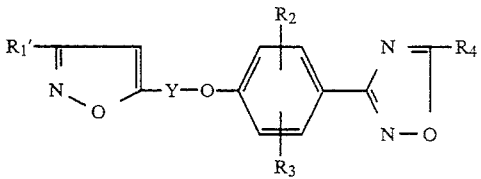

wherein $R_1'$ is tert-butyldimethylsilyloxyalkyl $[(CH_3)_3CSi(Me)_2$-O-alkyl] and Y, $R_2$, $R_3$ and $R_4$ are as defined above in this paragraph, by cleaving the tert-butyldimethylsilyl ether.

Cleavage of the tert-butyldimethylsilyl ether is carried out by treating compound XVII with strong organic acid, e.g., acetic acid or trifluoroacetic acid, or inorganic acid, e.g., hydrochloric acid or sulfuric acid, in an inert solvent, e.g., tetrahydrofuran or dioxane in the presence of water at a temperature in the range of from about 20° to about 60° C.

The compound of formula XVII where $R_4$ is dihalomethyl, trihalomethyl, cycloalkyl, alkoxyalkyl or 2,2,2trifluoroethyl, can be prepared by a process which comprises reacting phenol IV wherein $R_2$ and $R_3$ are as defined hereinbefore and $R_7$ is as defined above in this paragraph for $R_4$, with an isoxazole of the formula

or

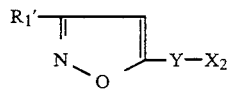

wherein $R_1'$, Y and $X_2$ are as defined hereinbefore.

The phenol IV is reacted with haloisoxazole XVI using a procedure similar to that described hereinbefore the preparation of cyano compound IX from cyanophenol VII and haloisoxaozle VIII.

The phenol IV is reacted with isoxazole XV in the presence of diethyl azodicarboxylate (DEAD) and triphenylphosphine in an inert solvent, e.g., tetrahydrofuran, chloroform, dimethylformamide or N-methylpyrrolidinone, at a temperature in the range of from about −20° to about 20° C.

The intermediate phenol IV can be prepared by the procedure described hereinbefore.

The intermediate isoxazoles XV and XVI can be prepared by reacting isoxazole X, wherein $R_1$ is hydroxyalkyl, with tert-butyldimethylsilyl chloride to give the corresponding tert-butyldimethylsilyl ether of formula

where $R_1'$ is as defined above, and reaction of an alkali metal derivative of compound XVIII with ethylene oxide or $X_2$—$Y'$—$X_2$ respectively.

Isoxazole X, wherein $R_1$ is hydroxyalkyl, is reacted with tert-butyl(dimethyl)silyl chloride in the presence of 4 (dimethylamino)pyridine and a base, e.g., triethylamine, pyridine or imidazole, in a dry inert solvent., e.g., methylene chloride, chloroform or tetrahydrofuran, at room temperature to give compound XVIII. Isoxazole XV is prepared by reacting an alkali metal derivative of compound XVIII with ethylene oxide, preferably in the presence of a chelating agent, e.g., N,N,N',N'-tetramethylethylenediamine or hexamethyl phosphoric triamide, in a dry inert solvent, e.g., tetrahydrofuran, at a temperature in the range of from about −78° to about 20° C. The alkali metal derivative is prepared in situ by reacting compound XVIII with an organo-alkali metal base, e.g., butyllithium or lithium diisopropylamide, under anhydrous conditions.

The compound of formula XVII, where $R_4$ is dihalomethyl, trihalomethyl, cycloalkyl, alkoxyalkyl or 2,2,2trifluoroethyl, can also be prepared, as can the compound of that formula where $R_4$ is amino, according to the following flow sheet:

Compound XXI is reacted with hydroxylamine hydrochloride in the presence of a base, e.g., sodium hydroxide, and water in an alcoholic solvent, e.g., methyl or ethyl alcohol, at a temperature in the range of from about 0° to about 25° C.

The intermediate compounds of formula XXI can be prepared by reacting an alkali metal derivative of compound III, wherein $R_6$ is as defined for $R_4$ of compound XXI, with an alkyl haloformate, $R_8OCOX$, where X is as defined hereinbefore. The reaction takes place in a dry inert solvent, e.g., tetrahydrofuran or dioxane, at an initial temperature of about −78° to about −20° C. with subsequent warming to about 20° to about 25° C. The alkali metal derivative can be prepared in situ by reacting compound III with an organo-alkali metal, e.g., butyllithium or lithium diisopropylamide, under anhydrous conditions.

Certain compounds of formula I are intermediates for other compounds of formula I as described hereinafter.

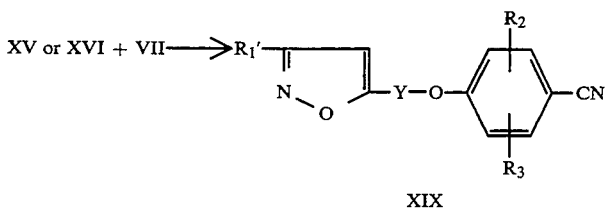

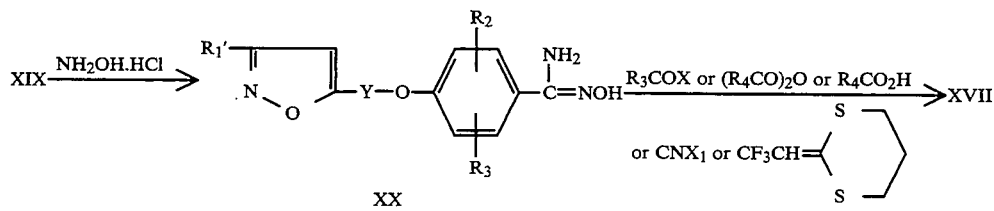

The reaction of compound XV or XVI with cyanophenol VII to give compound XIX is carried out by procedures similar to those described hereinbefore for preparing compound XVII by reacting phenol IV with isoxazole XV or haloisoxazole XVI respectively. The reaction of cyano compound XIX with hydroxylamine hydrochloride to give amidoxime XX, and the latter with the acid halide, acid anhydride, carboxylic acid, cyanogen halide or ketene 1,3-propanedithiol acetal to give compound XVII can be carried out by procedures similar to those described hereinbefore for preparing amidoxime V from cyano compound IX and for preparing the compound of formula I from amidoxime V.

The compounds of formula I wherein $R_1$ is hydroxy, Y, $R_2$ and $R_3$ are as defined hereinbefore, and $R_4$ is cycloalkyl or alkoxyalkyl can be prepared by reacting a compound of the formula

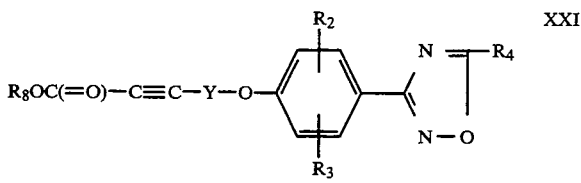

where $R_8$ is alkyl and Y, $R_2$, $R_3$ and $R_4$ are as defined above in this paragraph, with hydroxylamine hydrochloride to give the compound of formula I where $R_1$ is hydroxy.

The acid halides, alkyl haloformates and acid anhydrides used in the hereinbefore described processes for preparing the compounds of formula I and intermediates therefor, belong to well known classes of compounds and can be readily prepared by known procedures.

The compound of formula I wherein $R_1$ is alkyl, trifluoromethyl, cycloalkyl or alkoxyalkyl, Y, $R_2$, $R_3$ are as defined hereinabove, and $R_4$ is alkoxy or N=Q, where N=Q is alkylamino or dialkylamino, can be prepared from the corresponding compound of formula I wherein $R_4$ is trichloromethyl. In the case where $R_4$ is alkoxy, the trichloromethyl compound is reacted with an alkali metal alkoxide, e.g., sodium methoxide or sodium ethoxide, and in the case where $R_4$ is N=Q, with an amine(N=Q), in a suitable solvent, e.g., dimethylformamide or N-methylpyrrolidinone, at room temperature to give the corresponding compound of formula I where $R_4$ is alkoxy, alkylamino or dialkylamino.

The compounds of formula I wherein $R_1$ is hydroxyalkyl, Y, $R_2$ and $R_3$ are as defined hereinbefore, and $R_4$ is hydroxy, dihalomethyl, trihalomethyl, cycloalkyl, hydroxyalkyl, 2,2,2-trifluoroethyl or amino, can be prepared from the corresponding compound wherein $R_1$ is alkoxyalkyl by ether cleavage of the alkoxyalkyl moiety. The alkoxyalkyl compound is treated with trimethylsilyl iodide in a dry inert solvent, e.g., 1,2-dichloroethane, chloroform or acetonitrile, at a temperature in the range of from about 60° to about 80° C. to give the corresponding hydroxyalkyl compound.

The compounds of formula I wherein $R_1$ is alkyl, alkoxy, trifluoromethyl, cycloalkyl or alkoxyalkyl, Y, $R_2$ and $R_3$ are as defined hereinbefore, and $R_4$ is CON=Q, where N=Q is amino, alkylamino or dialkylamino, can be prepared by reacting the corresponding compound of formula I wherein $R_4$ is alkoxycarbonyl with amine N=Q in a polar solvent, e.g., ethyl alcohol or N-methylpyrrolidinone, at room temperature to give the corresponding compound where $R_4$ is CON=Q.

The compound of formula I where $R_1$ is alkyl, alkoxy, trifluoromethyl, cycloalkyl or alkoxyalkyl, Y, $R_2$ and $R_3$ are as defined hereinbefore, and $R_4$ is cyano, can be prepared from the corresponding compound wherein $R_4$ is CON=Q, where N=Q is amino, by treating the latter with trifluoroacetic anhydride in the presence of a base, e.g., pyridine or triethylamine, in a dry inert solvent, e.g., tetrahydrofuran, chloroform or 1,2-dichloroethane, at a temperature in the range of from about 0° to about 20° C.

The compounds of formula I wherein $R_1$ is alkoxy or hydroxyalkoxy, Y, $R_2$ and $R_3$ are as defined above, and $R_4$ is alkoxy, trihalomethyl, cycloalkyl, alkoxyalkyl, 2,2,2-trifluoroethyl or dialkylamino, can be prepared by etherification of the corresponding compound of formula I wherein $R_1$ is hydroxy. The etherification takes place by reacting the hydroxy compound with an alkyl halide or hydroxyalkyl halide, where halide is bromide, chloride or iodide, in the presence of a base, e.g., potassium carbonate or sodium carbonate, in an inert dry solvent, e.g., acetone, butanone or acetonitrile, at a temperature in the range of from about 50° to about 90° C.

The compounds of formula I wherein $R_1$ is alkyl, cycloalkyl, hydroxyalkyl, alkoxyalkyl or hydroxyalkoxy, Y, $R_2$ and $R_3$ are as defined hereinbefore, and $R_4$ is hydroxyalkyl can be prepared by transesterification of the corresponding compound of formula I wherein $R_4$ is alkanecarbonyloxyalkyl. The transesterification is carried out by treating the alkanecarbonyloxyalkyl compound with an inorganic or organic base, e.g., potassium carbonate, sodium bicarbonate or triethylamine, in an alcoholic solvent, e.g., methyl or ethyl alcohol, at room temperature.

The compounds of formula I wherein $R_1$ is alkyl, cycloalkyl or hydroxyalkyl, Y, $R_2$ and $R_3$ are as defined hereinbefore, and $R_4$ is hydroxyalkyl, can also be prepared by ether cleavage of the corresponding compound of formula I wherein $R_4$ is alkoxyalkyl. The ether cleavage can be carried out by treating the alkoxy compound with trimethylsilyl iodide using a procedure similar to that described hereinbefore for preparing the compound of formula I wherein $R_4$ hydroxyalkyl.

The compound of formula I wherein $R_1$ is alkyl, alkoxy, cycloalkyl, hydroxyalkyl, alkoxyalkyl or hydroxyalkoxy, Y, $R_2$ and $R_3$ are as defined hereinbefore, and $R_4$ is iodomethyl, can be prepared from the corresponding compound of formula I wherein $R_4$ is chloromethyl by reaction with alkali metal iodide, e.g., sodium iodide. The reaction takes place by treating the chloromethyl compound with the alkali metal iodide, e.g., sodium or potassium iodide, in an inert solvent, e.g., acetone or butanone, at about 20° C.

The compounds of formula I wherein $R_1$ is alkyl, alkoxy, cycloalkyl or alkoxyalkyl, Y, $R_2$ and $R_3$ are as defined hereinbefore, and $R_4$ is (4-methylphenyl)sulfonyloxymethyl, are prepared from the corresponding compound of formula I wherein $R_4$ is hydroxymethyl by reaction with (4methylphenyl)sulfonyl halide, where halide is bromide, chloride or iodide, in the presence of an inorganic base, e.g., potassium carbonate or sodium bicarbonate. The reaction takes place by reacting the reactants in an inert solvent, e.g., methylene chloride, chloroform or 1,2-dichloroethane, at about 20° C.

The compounds of formula I are sufficiently basic to form stable acid-addition salts with strong acids and such salts are within the purview of the invention. The nature of the acid-addition salt is immaterial, provided it is derived from an acid the anion of which is essentially non-toxic to animal organisms. Appropriate acid-addition salts include hydrochloride, hydrobromide, sulfate, acid sulfate, maleate, citrate, tartrate, methanesulfonate, p-toluenesulfonate, dodecyl sulfate and cyclohexanesulfonate. The acid-addition salts are prepared by conventional methods known in the art.

In the various processes described hereinabove for the preparation of the compounds of the invention, it will be appreciated that the reactions should be carried out for a time sufficient to provide the desired product and that for any specific reaction type, the time of the reaction will depend upon one or more factors such as, e.g., the nature of the reactants, the solvent employed and/or the temperature at which the reaction is carried out.

The antiviral compounds of the invention are formulated for use by preparing a dilute solution or suspension in a pharmaceutically acceptable aqueous, organic or aqueous-organic medium for topical or parenteral administration by intravenous or intramuscular injection, or for intranasal or ophthalmic application; or are prepared in tablet, capsule, or aqueous suspension form with conventional excipients for oral administration.

The structures of the compounds of the invention were established by modes of synthesis and elementary analysis, and by infrared, nuclear magnetic resonance and/or mass spectra.

The invention is further illustrated but not limited by the following examples.

EXAMPLE 1 a) 3-(3-Methylisoxazol-5-yl)propyl alcohol 3,5-Dimethylisoxazole (220 g, 2.27 moles) in 2.2 L tetrahydrofuran under nitrogen was cooled with stirring to −75° C. and 908 mL of 2.5M n-butyllithium (2.27 moles) in hexanes were added over 1 hour keeping the temperature at or less than 65° C. The chilled solution was stirred for thirty minutes after addition was complete and was then treated at about −70° C. with a solution of 112 g (2.54 moles) of ethylene oxide in 390 ml tetrahydrofuran over a period of 1.5 hours, keeping the temperature at about −65° C. and stirred overnight. The mixture at 8° C. was quenched with continued cooling in an 8° C. bath by adding 1.2 L of 2.5M hydrochloric acid over a period of 20 minutes, during which time the temperature rose to 23° C., and was stirred for 10 minutes. The organic phase was separated, washed with 500 ml of water and concentrated to give 147 g of title compound as a brown oil. The combined aqueous phases (original+wash phase) were extracted with methyl tert-butyl ether (3×200 ml) and the combined organic extracts were concentrated to give an additional 125 g of title compound as a brown oil.

b) 3-(3-Methylisoxazol-5-yl)propyl chloride

To the product from part (a) (125 g, 0.885 mole) in 1225 ml methylene chloride was added 192 ml (2.63 moles) of thionyl chloride over a period of 1 hour during which time the temperature rose to 40° C. to a gentle reflux. Heating at reflux was continued for 3 hours, the reaction mixture was allowed to stand overnight, and then heating at reflux was continued for 1 hour. The reaction mixture was added as a steady stream to 3 kg of ice water with vigorous stirring, stirring was continued for 1 hour and the aqueous phase was separated. Water (1 L) was added to the organic phase followed by 161 g of solid sodium bicarbonate in portions with vigorous stirring. The organic phase was separated and concentrated in vacuo to give a black oil which was purified by wiped-film distillation to give 94 g of the title compound as a yellow oil, bp 65° C./0.09 mm.

c) 3,5-Dimethyl-4-[3-(3-methylisoxazol-5-yl)propyloxy]-benzonitrile

A mixture of 3,5-dimethyl-4-hydroxybenzonitrile (7.36 g, 50.0 mmol), dry N-methylpyrrolidinone (100 mL), milled potassium carbonate (13.8 g, 100 mmol), potassium iodide (0.84 g, 5.0 mmol), and the product from part (b) (12.0 g, 75.0 mmol) was stirred at 60° C. for 18 hours. After cooling to room temperature, the mixture was partitioned between 200 mL water and 100 mL ethyl acetate. The aqueous layer was extracted twice with 50 mL portions of ethyl acetate. The combined organic extracts were washed with water, brine, dried (MgSO$_4$), and concentrated in vacuo to provide 18.3 g of a yellow oil. MPLC (Silica Gel 60 50×460 mm, 25% ethyl acetate in hexanes) provided 12.7 g (94.1%) of pure title compound as a white solid, m.p. 46°–48° C. (methanol).

d) 3,5-Dimethyl-4-[3-(3-methylisoxazol-5-yl)propyloxy]-N-hydroxybenzenecarboximidamide A mixture of the product prepared according to part (c) (18.4 g, 68.1 mmol), absolute ethanol (200 mL), milled potassium carbonate (46.9 g, 0.340 mol), and hydroxylamine hydrochloride (23.6 g, 0.340 mol) was refluxed for 18 hours. The hot mixture was filtered and the solids remaining washed with hot ethanol. The combined filtrates were concentrated in vacuo to provide 19.4 g (93.9%) of the title compound as a white powder which was of sufficient purity to be used in subsequent steps. A sample was recrystallized from ethanol to give a white solid, m.p. 129°–130.5° C.

e) 5-{3-[2.6-Dimethyl-4-(5-trifluoromethyl-1,2,4-oxadiazol-3-yl)phenoxy]propyl}-3-methylisoxazole [I; R$_1$=CH$_3$, Y=(CH$_2$)$_3$, R$_2$ and R$_3$=2,6-(CH$_3$)$_2$, R$_4$=CF$_3$]

To a solution of the product from part (d) (4.38 g, 14.4 mmol) in 8.0 mL dry pyridine was added 4.07 mL (28.8 mmol) of trifluoroacetic anhydride at a rate to maintain a gentle reflux. After addition was complete, the mixture was allowed to cool to room temperature, and diluted with water. The solids obtained were washed with water, dried in vacuo, and purified by chromatography (Silica Gel 60, 15–40% ethyl acetate in hexanes), to give 4.76 g of pure title compound as a white solid, m.p. 61°–62° C.

EXAMPLE 2 a) 3,5-Difluoro-4-hydroxybenzonitrile

A mixture of 4-bromo-2,6-difluorophenol (4.00 g, 19.0 mmol), copper (I) cyanide (1.72 g, 19.0 mmol), and dimethylformamide (40 mL) was refluxed for 6 hours, cooled to room temperature, diluted with water (150 mL), and filtered. The tan solids obtained were washed with water and retained. The combined filtrates were acidified (1N HCl) and extracted with ethyl acetate. The combined organic extracts were dried (MgSO$_4$), concentrated in vacuo, and purified by flash chromatography (Silica Gel 60, 20% ethyl acetate in hexanes) to give 1.03 g of pure title compound as an off-white solid, mp 195°–197° C.

The tan solid was suspended in ethyl acetate with a small amount of acetone, filtered, and concentrated in vacuo. The residue obtained was partitioned between ethyl acetate and 1N HCl. The aqueous phase was extracted with ethyl acetate and the combined organic phases purified as above to provide an additional 0.43 g (49% combined yield) of pure title compound.

The following compounds were prepared by a procedure similar to that of Example 1(c):

| Example | Compound |
| --- | --- |
| 2b | 3,5-Difluoro-4-[3-(3-methylisoxazol-5-yl)propyloxy]benzonitrile, mp 23–24.5° C. (ether/hexanes) - prepared from 3,5-difluoro-4-hydroxybenzonitrile and the product of Example 1b; yield 49.1%. |
| 3a | 3,5-Dichloro-4-[3-(3-methylisoxazol-5-yl)propyloxy]benzonitrile, mp 69.5–70.5° C. (methanol) (white solid) - prepared from 3,5-dichloro-4-hydroxybenzonitrile and the product of Example 1b; yield 80.7%. |

The following compounds were prepared by a procedure similar to that of Example 1d:

| Example | Compound |
| --- | --- |
| 2c | 3,5-Difluoro-4-[3-(3-methylisoxazol-5-yl)propyloxy]-N-hydroxybenzenecarboximidamide, mp 122–124° C. - prepared from the product of Example 2b; yield 86%. The crude product was purified by suspension in 10% ethanol in chloroform, filtration, concentration in vacuo and trituration of the resulting white solid in cold chloroform. |
| 3b | 3,5-Dichloro-4-[3-(3-methylisoxazol-5-yl)propyloxy]-N-hydroxybenzenecarboximidamide - prepared from the product of Example 3a (0.5 g). The product (0.78 g), obtained on concentration of the filtrates as an oily solid, was used in the next step. |

The following compounds were prepared by a procedure similar to that of Example 1e:

| Example | Compound |
| --- | --- |
| 2d | 5-{3-[2,6-Difluoro-4-(5-trifluoromethyl-1,2,4-oxadiazol-3-yl)phenoxy]propyl}-3-methylisoxazole [I; R$_1$ = CH$_3$, Y = (CH$_2$)$_3$, R$_2$ and R$_3$ = 2,6-(F)$_2$, R$_4$ = CF$_3$], mp 36–37° C. (hexanes) (white solid) - from the product of Example 2c and trifluoroacetic anhydride; yield 44.5%. |
| 3c | 5-{3-[2,6-Dichloro-4-(5-trifluoromethyl-1,2,4-oxadiazol-3-yl)phenoxy]propyl}-3-methylisoxazole [I; R$_1$ = CH$_3$, Y = (CH$_2$)$_3$, R$_2$ and R$_3$ = 2,6-(Cl)$_2$, R$_4$ = CF$_3$], mp 65–67° C. (hexanes) (white solid) - from the product of Example 3b and trifluoroacetic |

| Example | Compound |
|---|---|
| | anhydride; yield 80.5%. |
| 4 | 5-{3-[4-(5-Cyclopropyl-1,2,4-oxadiazol-3-yl)-2,6-dimethylphenoxy]propyl}-3-methylisoxazole [I; $R_1$ = $CH_3$, Y = $(CH_2)_3$, $R_2$ and $R_3$ = 2,6-$(CH_3)_2$, $R_4$ = cyclopropyl], mp 85–88° C. (methanol) (white solid) - from the product of Example 1d and cyclopropanecarbonyl chloride; yield 71.0%. |
| 5 | 5-{3-[2,6-Dimethyl-4-(5-methoxymethyl-1,2,4-oxadiazol-3-yl)phenoxy]propyl}-3-methylisoxazole [I; $R_1$ = $CH_3$, Y = $(CH_2)_3$, $R_2$ and $R_3$ = 2,6-$(CH_3)_2$, $R_4$ = $CH_2OCH_3$], mp 63–64° C. (ether/hexane) (white solid) - from the product of Example 1d and methoxyacetyl chloride; yield 76.1%. |
| 6 | 5-{3-[2,6-Dimethyl-4-(5-fluoromethyl-1,2,4-oxadiazol-3-yl)phenoxy]propyl}-3-methylisoxazole [I; $R_1$ = $CH_3$, Y = $(CH_2)_3$, $R_2$ and $R_3$ = 2,6-$(CH_3)_2$, $R_4$ = $CH_2F$], mp 80–80.5° C. (methanol) (white solid) - from the product of Example 1d and fluoroacetyl chloride; yield 45.6%. |
| 7 | 5-{3-[2,6-Dimethyl-4-(5-ethoxycarbonyl-1,2,4-oxadiazol-3-yl)phenoxy]propyl}-3-methylisoxazole [I; $R_1$ = $CH_3$, Y = $(CH_2)_3$, $R_2$ and $R_3$ = 2,6-$(CH_3)_2$, $R_4$ = $CO_2CH_2CH_3$], mp 105–106° C. (ethyl acetate/hexane) (white solid) - from the product of Example 1d and ethyl oxalyl chloride; yield 67.8%. |

EXAMPLE 8

5-{3-[2,6-Dimethyl-4-(5-oxo-4,5-dihydro-1,2,4-oxadiazol-3-yl)phenoxy]propyl}-3-methylisoxazole [tautomer of I where $R_1=CH_3$, Y=$(CH_2)_3$, $R_2$ and $R_3=2,6-(CH_3)_2$, $R_4=OH$]

To a chilled (0° C.) suspension of the product from Example 1d (3.03 g, 10.0 mmol), dry acetone (30 mL) and finely divided potassium carbonate (1.52 g, 11 mmol) was added dropwise a solution of ethyl chloroformate (1.05 mL, 11.0 mmol) in acetone (5.5 mL). After stirring at 0° C. for 1 hour, the reaction mixture was diluted with water (100 mL) and extracted with methylene chloride (3×25 mL). The combined organic extracts were washed with brine, dried (MgSO4), filtered through a short column of Florisil, and concentrated in vacuo to give the crude intermediate O-acyl derivative as an off-white solid which was then heated at 120°–130° C. for 45 minutes to give the title compound (2.38 g, 75.4%), mp 194°–195° C. (methanol) (white needles).

The following compounds were prepared by a procedure similar to that of Example 8:

| Example | Compound |
|---|---|
| 9 | 5-{3-[2,6-Dimethyl-4-(5-methylcarbonyloxymethyl-1,2,4-oxadiazol-3-yl)phenoxy]propyl}-3-methylisoxazole [I; $R_1$ = $CH_3$, Y = $(CH_2)_3$, $R_2$ and $R_3$ = 2,6-$(CH_3)_2$, $R_4$ = $CH_2OCOCH_3$], mp 71–73° C. (ether/hexanes) (white solid) - from the product of Example 1d and acetoxyacetyl chloride; yield 71.3%. The crude product was purified by chromatography (Silica Gel 60, 35% ethyl acetate in hexanes). |
| 10 | 5-{3-[4-(5-Chloromethyl-1,2,4-oxadiazol-3-yl)-2,6-dimethylphenoxy]propyl}-3-methylisoxazole [I; $R_1$ = $CH_3$, Y = $(CH_2)_3$, $R_2$ and $R_3$ = 2,6-$(CH_3)_2$, $R_4$ = $CH_2Cl$], mp 75–76° C. (methanol) (white solid) - from the product of Example 1d and chloroacetyl chloride. The crude product was purified by chromatography (Silica Gel 60, 20% ethyl acetate in hexanes); yield 76.2%. |
| 11 | 5-{3-[2,6-Dimethyl-4-(5-(1-methylcarbonyloxyethyl)-1,2,4-oxadiazol-3-yl)phenoxy]propyl}-3-methylisoxazole [I; $R_1$ = $CH_3$, Y = $(CH_2)_3$, $R_2$ and $R_3$ = 2,6-$(CH_3)_2$, $R_4$ = $CH(CH_3)OCOCH_3$], mp 77–77.5° C. (white solid) - from the product of Example 1d and 2-acetoxypropionyl chloride; yield 64.6%. |

EXAMPLE 12

5-{3-[2,6-Dimethyl-4-(5-trichloromethyl-1,2,4-oxadiazol-3-yl)phenoxy]propyl}-3-methylisoxazole [I; $R_1=CH_3$, Y=$(CH_2)_3$, $R_2$ and $R_3=2,6-(CH_3)_2$, $R_4=CCl_3$]

Trichloroacetic acid (22.8 g, 140 mmol) was added to the product of Example 1d (10.6 g, 34.8 mmol) and heated at 85° C. until a thick solution was obtained. Trichloroacetyl chloride (14.5 mL, 69.6 mmol) was added in three equal portions. A vigorous reaction ensued after addition of the first portion. The mixture was heated an additional hour at 94° C. The cooled mixture was diluted with water and extracted with ethyl acetate (3×25 mL). The combined organic phases were washed with saturated sodium bicarbonate, brine, dried (MgSO4) and concentrated in vacuo to give 10.1 g of orange oil. Chromatography (Silica Gel 60, methylene chloride) provided 6.94 g of yellow oil which was crystallized from methanol to give 5.03 g of pure title compound as white needles, mp 77°–77.5° C.

EXAMPLE 13

5-{3-[4-(5-Dichloromethyl-1,2,4-oxadiazol-3-yl)-2,6-dimethylphenoxy]propyl}-3-methylisoxazole [I; $R_1=CH_3$, Y=$(CH_2)_3$, $R_2$ and $R_3=2,6-(CH_3)_2$, $R_4=CHCl_2$]

Dichloroacetic acid (1.24 mL, 15.0 mmol) was added to the product of Example 1d (1.14 g, 3.76 mmol) and heated at 85° C. until a solution was obtained. Dichloroacetic anhydride (1.14 mL, 7.52 mmol) was added dropwise rapidly and stirred at 85° C. for an additional hour. Work-up as described for Example 12 provided 1.51 g of yellow-brown oil which was purified by chromatography (Silica Gel 60, 25% ethyl acetate in hexanes) to give 1.37 g (91.3%) of pure title compound as a pale yellow oil which solidified upon standing, mp 52°–3° C. (ethanol).

EXAMPLE 14

5-{3-[4-(5-Difluoromethyl-1,2,4-oxadiazol-3-yl),2,6-dimethylphenoxy]propyl}-3-methylisoxazole [I; $R_1=CH_3$, Y=$(CH_2)_3$, $R_2$ and $R_3=2,6$-dimethyl, $R_4=CHF_2$)

Difluoroacetic acid (0.31 mL, 5.0 mmol) was added to a cold (−25° C.) solution of 1,1'-carbonyldiimidazole (0.80 g, 5.0 mmol) in dry tetrahydrofuran (5.0 mL). After 5 minutes, the resulting suspension was added dropwise rapidly to a solution of the product of Example 1d in dry tetrahydrofuran (20 mL). The mixture was refluxed for 2 hours, cooled, diluted with water, and extracted with ethyl acetate (3×). The combined organic phases were washed with water, brine, dried (MgSO4), and concentrated in vacuo to give 0.78 g of a pale yellow solid. Chromatography (Silica Gel 60, 30% ethyl acetate in hexanes) provided 0.55 g of pure title compound as a pale yellow oil which solidified upon standing, mp 70.5°–71° C. (methanol).

EXAMPLE 15

5-{3-[4-(5-Imino-4,5-dihydro-1,2,4-oxadiazol-3-yl)2,6-dimethylphenoxy]propyl}-3-methylisoxazole [tautomer of I where $R_1=CH_3$, $Y=(CH_2)_3$, $R_2$ and $R_3=2,6$-$(CH_3)_2$, $R_4=NH_2$]

Cyanogen bromide (1.17 g, 11.0 mmol) was added in portions to a mixture of the product of Example 1d (3.03 g, 10.0 mmol) and potassium bicarbonate (1.10 g, 11.0 mmol) in 50% aqueous ethanol (8.0 mL). After 15 minutes, the thick yellow suspension was diluted with water and filtered. The yellow solid obtained was washed with water and ether to give 1.48 g (45.1%) of pure title compound as a yellow powder, mp 175°–183° C.

EXAMPLE 16

5-{3-[2,6-Dimethyl-4-(5-methoxy-1,2,4-oxadiazol-3-yl)phenoxy]propyl}-3-methylisoxazole [I; $R_1=CH_3$, $Y=(CH_2)_3$, $R_2$ and $R_3=2,6$-$(CH_3)_2$, $R_4=OCH_3$]

The product of Example 12 (627 mg, 1.46 mmol) was added to a freshly prepared solution of sodium methoxide in methanol (1.5 equivalents sodium in 5 mL methanol) in dry dimethylformamide (3–5 mL) and the mixture was stirred at room temperature for 15–30 minutes. The reaction mixture was diluted with water and extracted with ethyl acetate (3×). The combined organic extracts were washed with water, brine, dried (MgSO4) and concentrated in vacuo. The crude residue (0.64 g) was purified by chromatography (Silica Gel 60, first with 2% methanol in methylene chloride followed by 5% ethyl acetate in methylene chloride) to give pure title compound (308) as a colorless oil which crystallized from methanol, mp 64.5°–65.5° C. (white solid).

EXAMPLE 17

5-{3-[2,6-Dimethyl-4-(5-ethoxy-1,2,4-oxadiazol-3-yl)phenoxy]propyl}-3-methylisoxazole [I; $R_1=CH_3$, $Y=(CH_2)_3$, $R_2$ and $R_3=2,6$-$(CH_3)_2$, $R_4=OCH_2CH_3$]

Following the procedure of Example 16 but using sodium ethoxide in ethanol in place of sodium methoxide in methanol there was obtained from the product of Example 12 (905 mg, 2.10 mmol) a crude residue (0.82 g) which was purified by chromatography (Silica Gel 60, 2% ethyl acetate in methylene chloride) to give 0.52 g (69%) of pure title compound as a yellow solid, mp 70°–72.5° C. (ethanol).

EXAMPLE 18

5-{3-[2,6-Dimethyl-4-(5-methylimino-4,5-dihydro-1,2,4-oxadiazol-3-yl)phenoxy]propyl}-3-methylisoxazole [tautomer of I where $R_1=CH_3$, $Y=(CH_2)_3$, $R_2$ and $R_3=2,6$-$(CH_3)_2$, $R_4=NHCH_3$]

The product of Example 12 (1.00 g, 2.32 mmol) was added to 5 ml of 40% aqueous methylamine in dimethylformamide (3–5 mL) and the mixture was stirred at room temperature for 18 hours. The reaction mixture was diluted with water and extracted with ethyl acetate (3×). The combined organic extracts were washed with water, brine, dried (MgSO4) and concentrated in vacuo. The crude residue (0.54 g) was purified by chromatography (Silica Gel 60, first with 2% methanol in methylene chloride and then with 50% ethyl acetate in hexanes) to give 300 mg (37.5%) of pure title compound as a yellow solid, mp 126.5°–127° C. (ethanol).

EXAMPLE 19

5-{3-[2,6-Dimethyl-4-(5-dimethylamino-1,2,4-oxadiazol-3-yl)phenoxy]propyl}-3-methylisoxazole [I; $R_1=CH_3$, $Y=(CH_2)_3$, $R_2$ and $R_3=2,6$-$(CH_3)_2$, $R_4=N(CH_3)_2$]

Following the procedure of Example 18 but using 40% aqueous dimethylamine in place of 40% aqueous methyl amine and reducing the reaction time to 15–30 minutes, there was obtained from the product of Example 12 (0.97 g, mmol) a crude residue (0.75 g) which was purified by chromatography (Silica Gel 60, 50% ethyl acetate/hexanes) give 0.70 g (84%) of pure title compound as a pale yellow solid, mp 123°–124° C. (ethanol).

EXAMPLE 20 a) 3,5-Dimethyl-4-(3-ethinylpropoxy)benzonitrile

Following the procedure of Example 1c and using 14.7 g (100 mmol) of 3,5-dimethyl-4-hydroxybenzonitrile and substituting 5-chloro-1-pentyne (12.7 mL, 120 mmol) for the product of Example 1b, there was obtained a red-brown oil which was purified by chromatography (Silica Gel 60, 15% ethyl acetate in hexanes) to give pure title compound (21.2 g, 99.4%) as a pale yellow oil.

b) 3,5-Dimethyl-4-(3-ethinylpropoxy)-N-hydroxybenzenecarboximidamide

Following the procedure of Example 1d and using 13.0 g (61.0 mmol) of the product from part (a), there was obtained the title compound (14.9 g, 99.3%) as a white solid which was sufficiently pure for use in the next step.

c) 3-[3,5-Dimethyl-4-(3-ethinylpropoxy)phenyl]-5-trifluoromethyl-1,2,4-oxadiazole Following the procedure of Example 1e and using 7.40 g (30.0 mmol) of the product of part (b), 9.0 mL of dry pyridine and 8.50 mL of trifluoroacetic anhydride there was obtained pure title compound (6.42 g, 65.9%) as a pale yellow oil which crystallized from methanol to give the title compound as a white solid, mp 45.5°–48° C.

Procedure 1—general procedure for preparing the compounds of Examples 21, 22, 23, 28a and 29a below To a solution of N-chlorosuccinimide (NCS, 1.8–2.5 equivalents) in dry N,N-dimethylformamide or N-methylpyrrolidinone (1.6–3.0 mL per mmol NCS) and 1–2 drops of pyridine was added dropwise a solution of oxime (1.8–2.5 equivalents) in the same solvent (0.40–0.80 mL per mmol oxime). The internal temperature was maintained at 25°–30° C. with a 25° C. water bath. After 1 hour at room temperature, a solution of the appropriate ethinyl compound (formula III or XII) (1 equivalent) in the same solvent (0.80 mL per mmol the ethinyl compound) was added. The reaction mixture was heated to 85°–90° C. and a solution of triethylamine (TEA, 1.8–2.5 equivalents) in the same solvent (0.80–1.6 mL per mmol TEA) was added dropwise over 45–90 minutes. After an additional hour at 85°–90° C., the mixture was cooled to room temperature, diluted with water, and extracted with ethyl acetate (3×). The combined organic phases were washed with 10% KHSO$_4$, water, brine, dried (MgSO$_4$ or Na$_2$SO$_4$) and concentrated in vacuo. The crude product was purified by chromatography (Silica Gel 60, 15–40% ethyl acetate in hexanes).

The following compounds were prepared by Procedure 1:

| Example | Compound |
|---|---|
| 21 | 5-{3-[2,6-Dimethyl-4-(5-trifluoromethyl-1,2,4-oxadiazol-3-yl)phenoxy]propyl}-3-(methoxymethyl)-isoxazole [I; R$_1$ = CH$_2$OCH$_3$, Y = (CH$_2$)$_3$, R$_2$ and R$_3$ = 2,6-(CH$_3$)$_2$, R$_4$ = CF$_3$], colorless oil (yield 70.1%) - from the product of Example 20c (2.00 g, 6.17 mmol) and methoxyacetaldehyde oxime (1.10 g, 12.3 mmol). |
| 22 | 5-{3-[2,6-Dimethyl-4-(5-trifluoromethyl-1,2,4-oxadiazol-3-yl)phenoxy]propyl}-3-(ethoxymethyl)-isoxazole [I; R$_1$ = CH$_2$OCH$_2$CH$_3$, Y = (CH$_2$)$_3$, R$_2$ and R$_3$ = 2,6-(CH$_3$)$_2$, R$_4$ = CF$_3$], mp 24–25° C. (methanol) (white powder) (yield 35.3%) - from the product of Example 20c (2.00 g, 6.17 mmol) and 2-ethoxyacetaldehyde oxime (1.27 g, 12.3 mmol). |
| 23 | 3-Cyclopropyl-5-{3-[2,6-dimethyl-4-(5-trifluoromethyl-1,2,4-oxadiazol-3-yl)phenoxy]propyl}-isoxazole [I; R$_1$ = cyclopropyl, Y = (CH$_2$)$_3$, R$_2$ and R$_3$ = 2,6-(CH$_3$)$_2$, R$_4$ = CF$_3$], mp 63.5–65° C. (ethanol) (white needles) (yield 82%) - from the product of Example 20c (0.92 g, 2.8 mmol) and cyclopropylcarboxaldehyde oxime (0.48 g, 5.6 mmol). |

2-Ethoxyacetaldehyde oxime (used in Example 22 above)

A solution of hydroxylamine hydrochloride (18.8 g, 0.270 mol), ethanol (25 mL), water (40 mL) and 1,1,2-triethoxyethane was warmed at 45° C. for 30 minutes, cooled to room temperature, and extracted with ether (3×). The combined organic phases were dried (MgSO$_4$), concentrated in vacuo, and filtered through a small plug of cotton to give 10.1 g of title compound as a pale yellow oil which was used as is.

EXAMPLE 24

5-Cyclopropyl-3-[3,5-dimethyl-4-(3-ethinylpropoxy)-phenyl]-1,2,4-oxadiazole

Following the procedure of Example 1e and using 5.00 g (20.3 mmol) of the product of Example 20b, 75 mL of dry pyridine and 2.77 mL (30.5 mmol) of cyclopropylcarbonyl chloride there was obtained pure title compound (3.98 g, 66.2%) as a nearly colorless oil which solidified on standing, mp 45°–46° C. (methanol).

Procedure 2—general procedure for preparing the compounds of Examples 25, 26 and 27 below To a chilled (0° C.) solution of the appropriate aldehyde oxime (2.5 equivalents) in dry dimethylformamide (DMF) (15 mL) was added in 1 portion N-chlorosuccinimide (NCS) (2.5 equivalents). After 1–2 hours, the product from Example 24 (1 equivalent) was added and the whole heated to 80° C. A solution of triethylamine (2.5 equivalents) in dry DMF (5 mL) was added dropwise over 90 minutes. The mixture was heated an additional 18 hours. Work up and purification as described for Example 21 provided the pure product.

The following compounds were prepared by Procedure 2:

| Example | Compound |
|---|---|
| 25 | 5-{3-[4-(5-Cyclopropyl-1,2,4-oxadiazol-3-yl)-2,6-dimethylphenoxy]propyl}-3-ethylisoxazole [I; R$_1$ = CH$_2$CH$_3$, Y = (CH$_2$)$_3$, R$_2$ and R$_3$ = 2,6-(CH$_3$)$_2$, R$_4$ = cyclopropyl], colorless oil - from the product of Example 24 and propionaldehyde oxime; yield 67%. |
| 26 | 5-{3-[5-(Cyclopropyl-1,2,4-oxadiazol-3-yl)-2,6-dimethylphenoxy]propyl}-3-(methoxymethyl)-isoxazole [I; R$_1$ = CH$_2$OCH$_3$, Y = (CH$_2$)$_3$, R$_2$ and R$_3$ = 2,6-(CH$_3$)$_2$, R$_4$ = cyclopropyl], mp 44–45° C. (methanol) (white solid) - from the product of Example 24 and methoxyacetaldehyde oxime; yield 26.1% (from combination of two runs). |
| 27 | 3-Cyclopropyl-5-{3-[5-(cyclopropyl-1,2,4-oxadiazol-3-yl)-2,6-dimethylphenoxy]propyl}isoxazole [I; R$_1$ = R$_4$ = cyclopropyl, Y = (CH$_2$)$_3$, R$_2$ and R$_3$ = 2,6-(CH$_3$)$_2$], mp 59–60° C. (methanol) (white solid) - from the product of Example 24 and cyclopropylcarboxaldehyde oxime; yield 60.4%. |

EXAMPLE 28 a)

3,5-Dimethyl-4-[3-(3-ethylisoxazol-5-yl)propyloxy]benzonitrile

Following Procedure 1 above but omitting the pyridine and using propionaldehyde oxime (8.6 g, 118 mmol) and the product of Example 20a (10.1 g, 47.0 mmol) there was obtained 4.90 g (36.7%) of pure title compound, mp 53.5°–54.5° C. (ethanol).

b)

3,5-Dimethyl-4-[3-(3-ethylisoxazol-5-yl)propyloxy]-N-hydroxybenzenecarboximidamide A mixture of the product from part (a) (2.01 g, 7.50 mmol), ethanol (20 mL), hydroxylamine hydrochloride (2.61 g, 37.5 mmol), and finely divided potassium carbonate (5.20 g, 37.5 mmol) was refluxed for 18 hours. The mixture was filtered hot, the filter cake washed with ethanol, and the combined filtrates concentrated in vacuo to give 2.57 g of crude title compound as a pasty yellow solid, which was used as such in the next step.

c)

5-{3-[2,6-Dimethyl-4-(5-trifluoromethyl-1,2,4-oxadiazol-3yl)-phenoxy]propyl}-3-ethylisoxazole [I; R$_1$=CH$_2$CH$_3$, Y=(CH$_2$)$_3$, R$_2$ and R$_3$=2,6-(CH$_3$)$_2$, R$_4$=CF$_3$]

All the product from part (b) was dissolved in pyridine (2.3 mL) and trifluoroacetic anhydride (2.1 mL, 15 mmol) was added dropwise. The mixture was refluxed for 1 hour, cooled to room temperature, diluted with water, and extracted with methylene chloride (3×). The combined organic phases were washed with 1N HCl, water, brine, dried (MgSO$_4$), and concentrated in vacuo. The pale yellow oil obtained (2.15 g) was chromatographed (Silica Gel 60, methylene chloride) to give 2.10 g (70.7%) of pure title compound as a white solid, mp 157°–158° C. (methanol).

EXAMPLE 29 a)

3,5-Dimethyl-4-{3-[3-(2-methoxyethyl)isoxazol-5-yl]propyloxy}benzonitrile

Following Procedure 1 above and using 3-methoxypropionaldehyde oxime (1.94 g, 18.8 mmol) and the product of Example 20a (2.20 g, 10.3 mmol) there was obtained 1.51 g (46.5%) pure title compound as a colorless oil which crystallized from ethanol as fine white needles, mp 64°–64.5° C. There was recovered 0.89 g (40.4%) of starting product of Example 20a.

b)
5-{3-[2,6-Dimethyl-4-(5-trifluoromethyl-1,2,4-oxadiazol-3-yl)phenoxy]propyl}-3-(methoxyethyl)isoxazole [I; $R_1=CH_2CH_2OCH_3$, $Y=(CH_2)_3$, $R_4=CF_3$]

Sodium (442 mg, 19.2 mg-atom) was dissolved in dry methanol (20 mL) contained in an addition funnel. This solution was added dropwise to a solution of hydroxylamine hydrochloride (1.34 g, 19.2 mmol) in dry methanol (10 mL). A fine white precipitate formed. After 1 hour, a solution of the product from part (a) (1.21 g, 3.85 mmol) in dry methanol (5 mL) was added and the mixture heated at reflux for 2.5 hours. The hot reaction mixture was filtered, the filter cake washed with methanol, and the combined filtrates concentrated in vacuo. The white oily solid obtained was dissolved in pyridine (4 mL) and trifluoroacetic anhydride (1.63 mL, 11.6 mmol) was added at a rate to maintain a gentle reflux. The mixture was heated at reflux for an additional 30 minutes, cooled to room temperature, diluted with water, and extracted with ethyl acetate (3×). The combined organic phases were washed with 10% KHSO$_4$, water, brine, dried (MgSO$_4$), and concentrated in vacuo to give 2.27 g of yellow oil. Chromatography (Silica Gel 60, 30% ethyl acetate in hexanes) provided 1.28 g (78.0%) of pure title compound as a colorless oil. Crystallization from methanol gave a white solid, mp 36.5°–37° C.

3-Methoxypropionaldehyde oxime (used in Example 29a above)

To a solution of hydroxylamine hydrochloride (2.80 g, 40.2 mmol), 10% aqueous sodium acetate (4.0 mL) and water (6 mL) was added 1,1,3-trimethoxypropane (2.12 mL, 14.9 mmol) and heated at 40°–50° C. for 30 minutes. After cooling to room temperature, the solution was saturated with sodium chloride and extracted with ether (3×) and methylene chloride (3×). The combined organic phases were dried (MgSO$_4$), filtered through a pad of Florisil, and concentrated in vacuo to provide 1.6 g of title compound as a colorless oil which was used as is.

Procedure 3—general procedure for the preparation of the compounds of Examples 30a and b, 31a and b, and 32a and b A mixture of the appropriate 4-hydroxybenzonitrile (1 equivalent), dry ethanol (3.7–8.9 mL per mmol of the 4-hydroxybenzonitrile), hydroxylamine hydrochloride (5 equivalents), and finely divided potassium carbonate (5 equivalents) was refluxed with efficient stirring for 18 hours. The hot reaction mixture was filtered and the filter cake washed with ethanol. The combined filtrates were concentrated in vacuo to give the crude amidoximes which were dissolved into pyridine (1–2 mL per mmol of the 4-hydroxybenzonitrile). Trifluoroacetic anhydride (5 equivalents) was added at a rate to maintain a gentle reflux. After heating an additional 0.5–3 hours, the cooled reaction mixture was diluted with ethyl acetate and water (4:1) until homogeneous. The organic phase was extracted with cold 1N KOH (3×). The basic extracts were acidified with concentrated HCl and extracted with ethyl acetate (3×). The combined organic phases were washed with brine, dried (MgSO$_4$), concentrated in vacuo. Chromatography (Silica Gel 60, ethyl acetate in hexanes or Florisil, methylene chloride) provided the pure 4-hydroxyphenyl-5-trifluoromethyl-1,2,4-oxadiazole.

Following Procedure 3 there were prepared the following crude intermediate amidoximes and corresponding 4-hydroxy-5-trifluoromethyl-1,2,4-oxadiazoles:

| Example | Compound |
| --- | --- |
| 30a | 3,5-Dimethyl-4,N-dihydroxybenzenecarboximidamide - from 3,5-dimethyl-4-hydroxybenzonitrile. |
| 30b | 3-(3,5-Dimethyl-4-hydroxyphenyl)-5-trifluoromethyl-1,2,4-oxadiazole, mp 114–115° C. (hexane) (white needles) - from the product of Example 30a; yield 75.2%. |
| 31a | 3,5-Dichloro-4,N-dihydroxybenzenecarboximidamide - from 3,5-dichloro-4-hydroxybenzonitrile. |
| 31b | 3-(3,5-Dichloro-4-hydroxyphenyl)-5-trifluoromethyl-1,2,4-oxadiazole, mp 96–98° C. (hexane) (white needles) - from the product of Example 31a; yield 52.0%. |
| 32a | 4,N-Dihydroxybenzenecarboximidamide - from 4-hydroxybenzonitrile. |
| 32b | 3-(4-Hydroxyphenyl)-5-trifluoromethyl-1,2,4-oxadiazole, mp 74–75° C. (hexanes) (white needles) - from the product of Example 32a; yield 56.4%. |

EXAMPLE 30c

5-{5-[2,6-Dimethyl-4-(5-trifluoromethyl-1,2,4-oxadiazol-3-yl)phenoxy]pentyl}-3-methylisoxazole [I; $R_1=CH_3$, $Y=(CH_2)_5$, $R_2$ and $R_3=2,6-(CH_3)_2$, $R_4=CF_3$]

Following a procedure similar to that of Example 1c but substituting the product from Example 30b (1.0 g, 3.9 mmol) for 3,5-dimethyl-4-hydroxybenzonitrile and 5-(3-methylisoxazol-5-yl)pentyl bromide (1.0 g, 4.3 mmol) for 3-(3-methylisoxazol-5-yl)propyl chloride and using 0.72 g (4.3 mmol) of potassium iodide there was obtained 0.25 g (16%) of pure title compound as a white solid, mp 41°–42° C. (methanol).

EXAMPLE 31c

5-{5-[2,6-Dichloro-4-(5-trifluoromethyl-1,2,4-oxadiazol-3-yl)phenoxy]pentyl}-3-methylisoxazole [I; $R_1=CH_3$, $Y=(CH_2)_5$, $R_2$ and $R_3=2,6-(Cl)_2$, $R_4=CF_3$]

Following a procedure similar to that of Example 1c but substituting the product from Example 31b (0.93 g, 3.1 mmol) for 3,5-dimethyl-4-hydroxybenzonitrile and 5-(3-methylisoxazol-5-yl)pentyl bromide (1.0 g, 4.3 mmol) for 3-(3-methylisoxazol-5-yl)propyl chloride and using 0.72 g (4.3 mmol) of potassium iodide there was obtained 0.83 g (60%) of pure title compound as a white solid, mp 42°–43° C. (hexanes).

EXAMPLE 32c

3-Methyl-5-{3-[4-(5-trifluoromethyl-1,2,4-oxadiazol-3-yl)phenoxy]propyl}isoxazole [I; $R_1=CH_3$, $Y=(CH_2)_3$, $R_2=R_3=H$, $R_4=CF_3$]

Following a procedure similar to that of Example 1c but substituting the product of Example 32b (0.42 g, 1.8 mmol) for 3,5-dimethyl-4-hydroxybenzonitrile and using 0.63 g (4.0 mmol) of the product of Example 1b and 0.67 g (4.0 mmol) of potassium iodide there was obtained, after trituration in cold methanol, 0.48 g (76%) of pure title compound as a white powder, mp 68°–69° C. (methylene chloride-hexanes).

EXAMPLE 33

5-{3-[2,6-Dimethyl-4-(5-trifluoromethyl-1,2,4-oxadiazol-3yl)-phenoxy]propyl}-3-(2-hydroxyethyl)isoxazole [I; $R_1=CH_2CH_2OH$, $Y=(CH_2)_3$, $R_2$ and $R_3=2,6-(CH_3)_2$, $R_4=CF_3$]

A solution of the product of Example 29b (1.28 g, 3.00 mmol), dry 1,2-dichloroethane (9 ml), and trimethylsilyl iodide (1.71 mL, 12.0 mmol) was refluxed for 4 hours. To the cooled reaction mixture was added methanol (8 mL). The mixture was diluted with water and extracted with ethyl acetate (3×). The combined organic phases were washed with 10% $NaHSO_3$, saturated $NaHCO_3$, brine, dried ($MgSO_4$), and concentrated in vacuo. Chromatography (Silica Gel 60, 50% ethyl acetate in hexanes) provided 1.11 g (90.2%) of pure title compound as a colorless oil which solidified upon standing, mp 74.5°–75° C. (methanol)(white solid).

EXAMPLE 34 a)

3-(tert-Butyldimethylsilyloxymethyl)-5-methylisoxazole

To a chilled (5° C.) solution of 3-hydroxymethyl-5-methylisoxazole (16.8 g, 148 mmol) and tert-butyldimethylsilyl chloride (24.6 g, 163 mmol) in dry methylene chloride (100 mL) was added over 15 minutes a solution of triethylamine (22.7 mL, 163 mmol) in methylene chloride (25 mL). 4-Dimethylaminopyridine (1.81 g, 14.8 mmol) was added and the thick reaction mixture was stirred at room temperature for 48 hours. Water (100 mL) was added and the aqueous layer extracted with methylene chloride (3×). The combined organic phases were washed with brine, dried ($MgSO_4$), filtered through a pad composed of a layer of Florisil and a layer of Silica Gel 60, and concentrated in vacuo. The yellow oil obtained (36.6 g) was purified by chromatography (Silica Gel 60, 2% ethyl acetate in hexanes) to give 27.7 g (81.9%) of pure title compound as a pale yellow oil.

b)

3-[3-(tert-Butyldimethylsilyloxymethyl)isoxazol-5-yl]propyl alcohol

To a cold (−78° C.) solution of the product from part (a) (13.0 g, 57.0 mmol) and N,N,N',N'-tetramethylethylenediamine (1.2 mL, 7.9 mmol) in dry tetrahydrofuran (THF) (150 mL) was added over 5 minutes n-butyllithium (31.3 mL, 2.0M in hexane). The bright orange-yellow anion solution was stirred for 25 minutes. Ethylene oxide (50.0 mL of 7.6M solution in dry THF) was added over 10 minutes. After 1.5 hours, saturated $NH_4Cl$ (30 mL) was added. The mixture was allowed to warm to room temperature and diluted with water. The aqueous layer was extracted with ethyl acetate (3×). The combined organic phases were washed with brine, dried ($MgSO_4$), filtered through a pad of Silica Gel 60, and concentrated in vacuo. Chromatography (Silica Gel 60, 20% ethyl acetate in hexanes) gave 3.44 g of recovered product from part (a) and 8.18 g (52.7%) of pure title compound as a colorless oil.

c)

3-(tert-Butyldimethylsilyloxymethyl)-5-{3-[2,6-dimethyl-4-(5-trifluoromethyl-1,2,4-oxadiazol-3-yl)phenoxy]-propyl}isoxazole A solution of the product from part (b) (1.00 g, 3.67 mmol), the product of Example 30b (1.04 g, 4.04 mmol), and triphenylphosphine (1.06 g, 4.04 mmol) in dry tetrahydrofuran (THF) (10 mL) was chilled to 0° C. A solution of diethyl azodicarboxylate (DEAD) (0.61 mL, 1.04 mmol) in dry THF (15 mL) was added dropwise over 20 minutes. The solution was stirred for 30 minutes at 0° C. and 18 hours at room temperature, diluted with water, and extracted with ethyl acetate (2×). The combined organic phases were washed with 10% NaOH, brine, dried ($MgSO_4$), filtered through a pad of Silica Gel 60, and concentrated in vacuo to give 3.44 g of yellow oil. Chromatography (Silica Gel 60, 10% ethyl acetate in hexanes) provided 1.73 g (83.6%) of pure title compound as a colorless oil.

d)

5-{3-[2,6-Dimethyl-4-(5-trifluoromethyl-1,2,4-oxadiazol-3-yl)phenoxy]propyl}-3-(hydroxymethyl)isoxazole [I; $R_1=CH_2OH$, $Y=(CH_2)_3$, $R_2$ and $R_3=2,6-(CH_3)_2$, $R_4=CF_3$]

A solution of the product from part (c) (0.75 g, 1.5 mmol), tetrahydrofuran (60 mL), and 1N HCl (7.5 mL) was stirred at room temperature for 18 hours and diluted with water (100 mL). The pH was adjusted to pH 7 (pH paper) with solid $NaHCO_3$ and extracted with ethyl acetate (3×). The combined organic phases were washed with brine, dried ($MgSO_4$), and concentrated in vacuo to give 0.73 g of yellow oil which was purified by chromatography (Silica Gel 60, 50% ethyl acetate in hexanes) to provide 0.58 g (100%) of pure title compound as a white solid, mp 92°–3° C. (white needles from ethanol).

EXAMPLE 35 a)

3,5-Dimethyl-4-{3-[3-(tert-butyldimethylsilyloxymethyl)isoxazol-5-yl]propyloxy}benzonitrile To a chilled (0° C.) methylene chloride (25 mL) solution of 3,5-dimethyl-4-hydroxybenzonitrile (773 mg, 5.26 mmol), the product from Example 34b (1.43 g, 5.26 mmol), and triphenylphosphine (1.38 g, 5.26 mmol) was added dropwise over 30 minutes a solution of diethyl azodicarboxylate (DEAD) (915 mg, 5.26 mmol) in methylene chloride (5 mL). The solution was stirred at 0° C. for 30 minutes and at room temperature for 18 hours, after which it was washed with water, 2.5M NaOH, brine, dried ($Na_2SO_4$) and concentrated in vacuo. The residue was triturated in ether to remove the bulk of the triphenylphosphine oxide, the filtrate concentrated in vacuo, and the residue purified by chromatography (Silica Gel 60, 15% ethyl acetate in hexanes) to give 1.73 g (82.2%) of pure title compound as a colorless oil.

b)

3,5-Dimethyl-4-{3-[3-(tert-butyldimethylsilyloxymethyl)isoxazol-5-yl]propyloxy}-N-hydroxybenzenecarboximidamide A mixture of the product from part (a) (1.22 g, 3.05 mmol), ethanol (30 mL), hydroxylamine hydrochloride (1.06 g, 15.2 mmol), and finely divided potassium carbonate (2.10 g, 15.2 mmol) was refluxed for 5 hours and filtered. The filter cake was washed with ethanol and the combined filtrates concentrated in vacuo to give 1.30 g of white solid. A portion of this material (0.78 g) was purified by chromatography (reverse phase silica gel, 17% water in methanol) to give 0.47 g of title compound which contained approximately 5% (NMR analysis) of desilylated material.

c)

5-{3-[4-(5-Cyclopropyl-1,2,4-oxadiazol-3-yl)-2,6-dimethylphenoxy]propyl}-3-(hydroxymethyl)isoxazole [I; $R_1=CH_2OH$, $Y=(CH_2)_3$, $R_2$ and $R_3=2,6\text{-}(CH_3)_2$, $R_4$=cyclopropyl]

To a solution of the purified product from part (b) (0.47 g, 1.1 mmol) in pyridine (20 mL) was added cyclopropylcarbonyl chloride (0.15 mL, 1.6 mmol). The mixture was heated at 90° C. for 26 hours. The pyridine was removed in vacuo and the residue partitioned between water and ethyl acetate. The aqueous phase was extracted with ethyl acetate (3×). The combined organic phases were washed with 3N HCl (2×), brine, dried ($Na_2SO_4$), and concentrated in vacuo to yield 0.61 g of a yellow oil. Chromatography (Silica Gel 60, 35% ethyl acetate in hexanes) provided 0.25 g (62%) of pure title compound as a colorless oil. Crystallization from methylene chloride and hexanes provided the title compound as a white solid, mp 80°–1° C.

EXAMPLE 36 a)

5-Cyclopropyl-3-[4-(5-ethoxycarbonyl-4-pentynyloxy)-3,5-dimethylphenyl]-1,2,4-oxadiazole To a cold (−78° C.) dry tetrahydrofuran solution (20 mL) of the product from Example 24 (1.30 g, 4.41 mmol) was added dropwise n-butyllithium (2.30 mL, 2.3M in hexane) over 15 minutes. After an additional 30 minutes at −78° C., ethyl chloroformate (0.63 mL, 6.6 mmol) was added and the mixture warmed gradually to 0° C. over 2 hours. The reaction was quenched with saturated $NH_4Cl$ and extracted with ethyl acetate (3×). The combined organic phases were washed with brine, dried ($Na_2SO_4$), and concentrated in vacuo to give a colorless oil (2.05 g). Chromatography (Silica Gel 60, 10–20% ethyl acetate in hexanes) provided 1.38 g (85.0%) of pure title compound as a colorless oil.

b)

5-{3-[4-(5-Cyclopropyl-1,2,4-oxadiazol-3-yl)-2,6-dimethylphenoxy]propyl}-3-hydroxyisoxazole [I; $R_1$=OH, $Y=(CH_2)_3$, $R_2$ and $R_3=2,6\text{-}(CH_3)_2$, $R_4$=cyclopropyl]

A mixture of the product from part (a) (810 mg, 2.20 mmol), ethanol (15 mL), hydroxylamine hydrochloride (400 mg, 5.76 mmol), and 10% NaOH (5 mL) was stirred at room temperature for 24 hours (after 8 hours, a solution was obtained). Water (6 mL) was added, the mixture acidified with concentrated HCl to pH 2 (pH paper), and extracted with ether (4×). The combined organic phases were washed with brine, dried ($Na_2SO_4$), and concentrated in vacuo to a white solid. Chromatography (Silica Gel 60, 50% ethyl acetate in hexanes) provided 0.55 g (70%) of pure title compound as a white solid, mp 155°–6° C. (ethyl acetate and hexanes).

EXAMPLE 37

5-{3-[4-(5-Cyclopropyl-1,2,4-oxadiazol-3-yl)-2,6-dimethylphenoxy]propyl}-3-ethoxyisoxazole [I; $R_1=OCH_2CH_3$, $Y=(CH_2)_3$, $R_2$ and $R_3=2,6\text{-}(CH_3)_2$, $R_4$=cyclopropyl]

A mixture of the product of Example 36b (0.30 g, 0.85 mmol), dry acetone (25 mL), finely divided potassium carbonate (0.24 g, 1.7 mmol), and ethyl iodide (0.18 mL, 2.2 mmol) was heated at 50° C. for 18 hours, filtered, and concentrated in vacuo to give a pinkish solid. Chromatography (Silica Gel, 50% ethyl acetate in hexanes) provided 0.19 g of slightly impure title compound and 0.12 g (37%) of a pure side product (the corresponding 2,3-dihydro-2-ethyl-3-oxoisoxazole compound) as a colorless oil. Pure title compound was obtained by chromatography (reverse silica gel, 20% water in methanol); yield 0.14 g (43%), mp 70°–1° C. (methanol).

EXAMPLE 38

5-{3-[4-(5-Aminocarbonyl-1,2,4-oxadiazol-3-yl)-2,6-dimethylphenoxy]propyl}-3-methylisoxazole [I; $R_1=CH_3$, $Y=(CH_2)_3$, $R_2$ and $R_3=2,6\text{-}(CH_3)_2$, $R_4=CONH_2$]

Finely divided product of Example 7 (3.08 g, 8.00 mmol) was added to 10% ethanolic ammonia (80 mL). After 15 minutes, a solution was obtained and a fine precipitate started to form. After 4 hours, the mixture was filtered and the solids obtained washed with cold ethanol to give 2.35 g (82.5%) of pure title compound as a fine white powder, mp 177°–8° C. (isopropyl acetate).

EXAMPLE 39

5-{3-[4-(5-Cyano-1,2,4-oxadiazol-3-yl)-2,6-dimethylphenoxy]propyl}-3-methylisoxazole [I; $R_1=CH_3$, $Y=(CH_2)_3$, $R_2$ and $R_3=2,6\text{-}(CH_3)_2$, $R_4=CN$]

To a chilled (0° C.) suspension of the product of Example 38 (1.60 g, 4.50 mmol) and dry pyridine (11.2 mL) in dry tetrahydrofuran (27 mL) was added trifluoroacetic anhydride (1.90 mL, 13.5 mmol). The mixture was stirred at 0° C. for 4 hours and at room temperature for 18 hours, diluted with water (100 mL), and extracted with ethyl acetate (2×25 mL). The combined organic phases were washed with 1N HCl (3×), brine, dried ($MgSO_4$), and concentrated in vacuo. The red solid obtained (1.67 g) was chromatographed (Silica Gel 60, 20% ethyl acetate in hexanes) to give 1.38 g (90.8%) of pure title compound as a white solid, mp 93°–4° C. (ethyl acetate and hexanes).

EXAMPLE 40

5-{3-[2,6-Dimethyl-4-(5-(hydroxymethyl)-1,3,4-oxadiazol-3-yl)phenoxy]propyl}-3-methylisoxazole [I; $R_1=CH_3$, $Y=(CH_2)_3$, $R_2$ and $R_3=2,6\text{-}(CH_3)_2$, $R_4=CH_2OH$]

A mixture of the product of Example 9 (4.12 g, 10.7 mmol) and finely divided potassium carbonate (1.48 g, 10.7 mmol) in dry methanol (40 mL) was stirred at room temperature for 15 minutes and partitioned between water (50 mL) and ethyl acetate (50 mL). The aqueous phase was extracted with ethyl acetate (1×25 mL) and the combined organic phases washed with brine, dried ($MgSO_4$), and concentrated in vacuo. Chromatography (Silica Gel 60, 50% ethyl acetate hexanes) provided 3.35 g (91.2%) of pure title compound as a white solid, mp 116.5°–117° C. (ether).

EXAMPLE 41

5-{3-[2,6-Dimethyl-4-(5-(iodomethyl)-1,2,4-oxadiazol-3-yl)phenoxy]propyl}-3-methylisoxazole [I; $R_1=CH_3$, $Y=(CH_2)_3$, $R_2$ and $R_3=2,6$-$(CH_3)_2$, $R_4=CH_2I$]

A solution of sodium iodide (0.45 g, 3.0 mmol) in dry acetone (5 mL) was added dropwise to a solution of the product of Example 10 (905 mg, 2.50 mmol) in dry acetone (5 mL). After 4 hours, the yellow suspension was poured into water (50 mL) and extracted with methylene chloride (3×25 mL). The combined organic phases were washed with brine, dried ($MgSO_4$), and concentrated in vacuo to give a brown oil (1.56 g). Filtration through Florisil (methylene chloride) provided a green-yellow oil (1.43 g) which solidified upon standing at 0° C. Chromatography (Silica Gel 60, 25% ethyl acetate in hexanes) provided 1.06 g (93.8%) of pure title compound as a pale yellow solid, mp 89°–90° C. (white needles from ether-pentane).

EXAMPLE 42

5-{3-[2,6-Dimethyl-4-(5-(4-methylphenylsulfonyloxymethyl)-1,2,4-oxadiazol-3-yl)phenoxy]propyl}-3-methylisoxazole [I; $R_1=CH_3$, $Y=(CH_2)_3$, $R_2$ and $R_3=2,6$-$(CH_3)_2$, $R_4=4CH_3C_6H_4SO_2OCH_2$)

To a chilled (0° C.) mixture of the product of Example 40 (343 mg, 1.00 mmol) and finely divided potassium carbonate (0.28 g, 2.0 mmol) in dry methylene chloride (5 mL) was added dropwise a filtered solution of p-toluenesulfonyl chloride (0.23 g, 1.2 mmol) in methylene chloride (2 mL). The mixture was stirred at room temperature for 72 hours, after which an additional 0.40 mmol of potassium carbonate and p-toluenesulfonyl chloride was added. After 24 hours, the mixture was partitioned between water (10 mL) and ethyl acetate (10 mL). The organic phase was washed with 1N NaOH (1×5 mL), brine, dried ($MgSO_4$), and concentrated in vacuo. Chromatography (Silica Gel 60, 40% ethyl acetate in hexanes) provided 478 mg (96.1%) of pure title compound as a white solid, mp 97°–8° C. (ether).

EXAMPLE 43

5-{3-[2,6-Dimethyl-4-(5-(2,2,2-trifluoroethyl)-1,2,4-oxadiazol-3-yl)phenoxy]propyl}-3-methylisoxazole [I; $R_1=CH_3$, $Y=(CH_2)_3$, $R_2$ and $R_3=2,6$-$(CH_3)_2$, $R_4=CH_2CF_3$]

A mixture of the product of Example 1d (4.55 g, 15.0 mmol), dry tetrahydrofuran (45 mL), 2-trifluoroethylidene-1,3 -dithiane (3.60 g, 18.0 mmol), and silver trifluoroacetate (7.3 g, 33 mmol) was refluxed in the dark for 22 hours, cooled to room temperature, and filtered. The green filter cake was washed with ethyl acetate (4×20 mL). The combined filtrates were concentrated in vacuo. The residue obtained was dissolved in methylene chloride (50 mL) and washed with water (3×25 mL), 0.1 M $NaHCO_3$ (freshly, prepared, 25 mL), brine, dried ($MgSO_4$), filtered through a pad of Florisil, and concentrated in vacuo to give 5.39 g of a yellow paste. Purification by chromatography (Silica Gel 60, 15% ethyl acetate in hexanes) provided 2.22 g (37.5%) of pure title compound as a white solid, mp 84°–85° C. (methanol) (white plates).

Example 44

5-{3-[4-(5-Cyclopropyl-1,2,4-oxadiazol-3-yl)-2,6-dimethylphenoxy]propyl}-3-(2-hydroxyethoxy)isoxazole [I; $R_1=HOCH_2CH_2O$, $Y=(CH_2)_3$, $R_2$ and $R_3=2,6$-$(CH_3)_2$, $R_4=$cyclopropyl)

A mixture of the product of Example 36b (0.75 g, 2.1 mmol), dry acetone (25 mL), finely divided potassium carbonate (0.32 g, 2.3 mmol), and 2-bromoethanol (0.19 mL, 2.7 mmol) was refluxed for 5 hours, filtered, and concentrated in vacuo to give a pinkish oil. Chromatography (Silica Gel 60, 50% ethyl acetate in hexanes) provided 0.51 g of impure title compound and 0.48 g (57%) of a pure side product (the corresponding 2,3-dihydro-2-(2-hydroxyethyl)-3-oxo-isoxazole compound) as a white solid. Pure title compound (0.31 g, 37%) was obtained by gradiant chromatography (Silica Gel 60, hexanes to 50% ethyl acetate in hexanes), mp 64°–65° C. (methylene chloride and hexanes).

Following a procedure similar to that of Example 1c but substituting for 3,5-dimethyl-4-hydroxybenzonitrile an equivalent amount of the following:

4-hydroxy-3-nitrobenzonitrile
4-hydroxy-3,5-dimethoxybenzonitrile
4-hydroxy-3-trifluoromethylbenzonitrile there can be obtained respectively the following compounds of formula IX:

4-[3-(3-methylisoxazol-5-yl)propyloxy]-3-nitrobenzonitrile
3,5-dimethoxy-4-[3-(3-methylisoxazol-5-yl)propyloxy]benzonitrile
4-[3-(3-methylisoxazol-5-yl)propyloxy]-3-(trifluoromethyl)benzonitrile.

Following a procedure similar to that of Example 1d but substituting for the product from Example 1c an equivalent amount of the above compounds of formula IX there can be obtained respectively the following compounds of formula V:

4-[3-(3-methylisoxazol-5-yl)propyloxy]-3-nitro-N-hydroxybenzenecarboximidamide
3,5-dimethoxy-4-[3-(3-methylisoxazol-5-yl)propyloxy]-N-hydroxybenzenecarboximidamide
4-[3-(3-methylisoxazol-5-yl)propyloxy]-3-trifluoromethyl-N-hydroxybenzenecarboximidamide.

Following a procedure similar to that of Example 1e but substituting for the product of Example 1d an equivalent amount of the above compounds of formula V there can be obtained respectively the following compounds of formula I:

3-methyl-5-{3-[2-nitro-4-(5-trifluoromethyl-1,2,4-oxadiazol-3-yl)phenoxy]propyl}isoxazole [I; $R_1=CH_3$, $Y=(CH_2)_3$, $R_2=2$-$NO_2$, $R_3=H$, $R_4=CF_3$]
5-{3-[2,6-dimethoxy-4-(5-trifluoromethyl-1,2,4-oxadiazol-3-yl)phenoxy]propyl}-3-methylisoxazole [I; $R_1=CH_3$, $Y=(CH_2)_3$, $R_2$ and $R_3=2,6$-$(OCH_3)_2$, $R_4=CF_3$]
3-methyl-5-{3-[2-trifluoromethyl-4-(5-trifluoromethyl-1,2,4-oxadiazol-3-yl)phenoxy]propyl}isoxazole [I; $R_1=CH_3$, $Y=(CH_2)_3$, $R_2=2$-$CF_3$, $R_3=H$, $R_4=CF_3$].

Following the procedures of Example 20a, b and c and using equivalent amounts of reactants in each case but substituting in Example 20a 11-chloro-1-undecyne for 5-chloro-1-pentyne there can be obtained successively the following:

3,5-dimethyl-4-(9-ethinylnonyloxy)benzonitrile;

3,5-dimethyl-4-(9-ethinylnonyloxy)-N-hydroxybenzenecarboximidamide; and

3-[3,5-dimethyl-4-(9-ethinylnonyloxy)phenyl]-5-trifluoromethyl-1,2,4-oxadiazole.

Following Procedure 1 and using equivalent amounts of acetaldehyde oxime and 3-[3,5-dimethyl-4-(9-ethinylnonyloxy)phenyl]-5-trifluoromethyl-1,2,4-oxadiazole, there can be obtained 5-{9-[2,6-dimethyl-4-(5-trifluoromethyl-1,2,4-oxadiazol-3-yl)phenoxy]nonyl}-3-methylisoxazole [I; $R_1=CH_3$, $Y=(CH_2)_9$, $R_2$ and $R_3=2,6\text{-}(CH_3)_2$, $R_4=CF_3$].

Following Procedure 1 and using equivalent amounts of n-hexyl aldehyde oxime and the product of Example 20c, there can be obtained 5-{3-[2,6-dimethyl-4-(5-trifluoromethyl)phenoxy]propyl}-3-(n-pentyl)isoxazole [I; $R_1=(CH_2)_4CH_3$, $Y=(CH_2)_3$, $R_1$ and $R_2=2,6\text{-}(CH_3)_2$, $R_4=CF_3$].

Following the procedure of Example 37 but substituting an equivalent amount of n-pentyl bromide for the ethyl iodide, there can be obtained 5-{3-[4-(5-cyclopropyl-1,2,4-oxadiazol-3-yl)phenoxy]propyl}-3-pentyloxyisoxazole [I; $R_1=O(CH_2)_4CH_3$, $Y=(CH_2)_3$, $R_1$ and $R_2=2,6\text{-}(CH_3)_2$. $R_4=$cyclopropyl].

Following the procedure of Example 37 but substituting equivalent amounts of the product of Example 40 and n-pentyl bromide for the product of Example 36b and ethyl iodide respectively, there can be obtained 5-{3-[2,6-dimethyl-4-(5-(n-pentyloxymethyl)-1,2,4-oxadiazol-3-yl)phenoxy]propyl}-3-methylisoxazole [I; $R_1=CH_3$, $Y=(CH_2)_3$, $R_2$ and $R_3=2,6\text{-}(CH_3)_2$, $R_4=CH_2O(CH_2)_4CH_3$].

Following the procedure of Example 1e but substituting an equivalent amount of cyclohexanecarbonyl chloride for the trifluoroacetic anhydride, there can be obtained 5-{3-[4-(5-cyclohexyl-1,2,4-oxadiazol-3-yl)-2,6-dimethylphenoxy]propyl}-3-methylisoxazole [I; $R_1=CH_3$, $Y=(CH_2)_3$, $R_1$ and $R_2=2,6\text{-}(CH_3)_2$, $R_4=$cyclohexyl].

Biological evaluation of representative compounds of formula I has shown that they possess antiviral activity. They are useful in inhibiting virus replication in vitro and are primarily active against picornaviruses, especially rhinoviruses. The in vitro testing of the representative compounds of the invention against picornaviruses showed that viral replication was inhibited at minimum inhibitory concentrations (MIC) ranging from 0.002 to 9.608 micrograms per milliliter. The test procedure used was as follows:

TEST PROCEDURE

The MIC values were determined by an automated tissue culture infectious dose 50% (TCID-50) assay. HeLa (Wisconsin) cells in 96-well cluster plates were infected with a dilution of virus which had been shown empirically to produce 80% to 100% cytopathic effect (CPE) in 3 days in the absence of drug. The compound to be tested was serially diluted through 10, 2-fold cycles and added to the infected cells. After a 3 day incubation at 33° C. and 2.5% carbon dioxide, the cells were fixed with a 5% solution of glutaraldehyde followed by staining with a 0.25% solution of crystal violet in water. The plates were then rinsed, dried, and the amount of stain remaining in the well (a measure of intact cells) was quantitated with an optical density reader. The MIC was determined to be the concentration of compound which protected 50% of the cells from virus-induced CPE relative to an untreated virus control.

In the above test procedures, representative compounds of formula I were tested against a panel of fifteen human rhinovirus (HRV) serotypes, namely, HRV-2, -14, -1A, -1B, -6, -21, -22, -15, -25, -30, -50, -67, -89, -86 and -41 and the MIC value, expressed in micrograms per milliliter (μg/ml), for each rhinovirus serotype was determined. The compounds tested were found to exhibit antiviral activity against one or more of these serotypes.

The MIC values (μg/ml) obtained for the compound of Example 1e in the above-described antiviral test procedure were as follows:

| HRV Serotype (MIC) | HRV Serotype (MIC) | HRV Serotype (MIC) |
|---|---|---|
| −2 (0.027) | −21 (0.015) | −50 (0.154) |
| −14 (0.022) | −22 (0.011) | −67 (0.070) |
| −1A (0.119) | −15 (0.147) | −89 (0.015) |
| −1B (0.054) | −25 (0.036) | −86 (0.029) |
| −6 not tested | −30 (0.047) | −41 (0.338) |

What is claimed is:

1. A process for preparing a compound of formula;

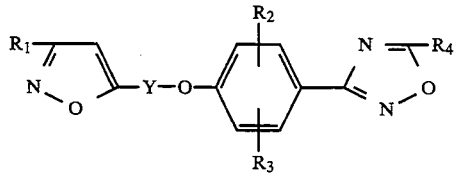

wherein;

$R_1$ is alkyl, alkoxy, cycloalkyl or alkoxyalkyl;

Y is alkylene of 3 to 9 carbon atoms, $R_2$ and $R_3$ independently are hydrogen, alkyl, alkoxy, halo, trifluoromethyl or nitro;

$R_4$ is 2,2,2-trifluoroethyl, which comprises reacting a compound of formula

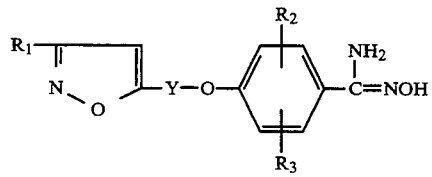

wherein R1, R2 and R3 are as described above with 2-trifluoroethylidene-1,3-dithiane in the presence of silver trifluoroacetate.

* * * * *